(12) United States Patent
Imai et al.

(10) Patent No.: US 7,785,524 B2
(45) Date of Patent: Aug. 31, 2010

(54) METHOD FOR ESTIMATING STATE OF ULTRAVIOLET CURING RESIN MATERIAL

(75) Inventors: Kiyoshi Imai, Kyoto (JP); Hiroyuki Inoue, Kyoto (JP); Tadashi Senga, Kyoto (JP); Kenichi Nakamune, Kyoto (JP); Yoji Hasebe, Kyoto (JP)

(73) Assignee: Omron Corporation, Kyoto (JP)

( * ) Notice: Subject to any disclaimer, the term of this patent is extended or adjusted under 35 U.S.C. 154(b) by 515 days.

(21) Appl. No.: 11/717,785

(22) Filed: Mar. 14, 2007

(65) Prior Publication Data

US 2007/0216069 A1 Sep. 20, 2007

(30) Foreign Application Priority Data

Mar. 15, 2006 (JP) ............................. P2006-071580

(51) Int. Cl.
*B29C 35/18* (2006.01)
*G01N 21/64* (2006.01)

(52) U.S. Cl. ..................... 264/408; 264/409; 264/494; 264/40.1; 250/459.1

(58) Field of Classification Search ................. 264/408, 264/494, 406, 409, 40.1; 250/459.1, 461.1
See application file for complete search history.

(56) References Cited

U.S. PATENT DOCUMENTS 5,037,763 A * 8/1991 Petisce ........................ 436/172
5,606,171 A * 2/1997 Neckers et al. ........... 250/459.1
5,962,857 A * 10/1999 McKeever et al. ........ 250/484.5
2006/0044555 A1 * 3/2006 Wang et al. ................. 356/301

FOREIGN PATENT DOCUMENTS

EP          1 308 477        5/2003
JP           2651036         5/1997
WO       WO-84/00066        1/1984

OTHER PUBLICATIONS

Moon et al., "A study on UV-curable adhesives for optical pick-up: I. Photo-initiator effects", International Journal of Adhesion & Adhesives, vol. 25, pp. 301-312, 2004.*

(Continued)

*Primary Examiner*—Joseph S Del Sole
*Assistant Examiner*—Robert Dye
(74) *Attorney, Agent, or Firm*—Foley & Lardner LLP

(57) ABSTRACT

A CPU provides a fluorescent light detecting head with an irradiation instruction, in response to which the fluorescent light detecting head irradiates an ultraviolet ray for detection on an ultraviolet curing resin material to be examined. The CPU then acquires from the fluorescent light detecting head an intensity of a fluorescent light emitted from a photo polymerization initiator included in the ultraviolet curing resin material when receiving the ultraviolet ray for detection. The CPU retrieves a predetermined number of past data of the intensity of the fluorescent light from a storage unit and performs a (moving) average calculation processing to calculate the intensity of the fluorescent light at the current time. The CPU performs an estimation processing of a state of the ultraviolet curing resin material based on the calculated intensity of the fluorescent light.

13 Claims, 19 Drawing Sheets

OTHER PUBLICATIONS

Decker, "Kinetic Study and New Applications of UV Radiation Curing", Macromolecular Rapid Communications, vol. 23, Issue 18, pp. 1067-1093, 2002, Published online: Jan. 22, 2003.*

Peinado et al., "Ultraviolet Curing of Acrylic Systems: Real-Time Fourier Transform Infrared, Mechanical, and fluorescence Studies," Journal of Polymer Science: Part A: Polymer Chemistry, vol. 40, pp. 4236-4244, 2002.*

Paik et al., "Fiberoptic Intrinsic Fluorescence for In-Situ Cure Monitoring of Amine Cured Epoxy and Composites," Polymer Engineering & Science, vol. 34, No. 12, pp. 1025-1032, Jun. 1, 1994.

* cited by examiner

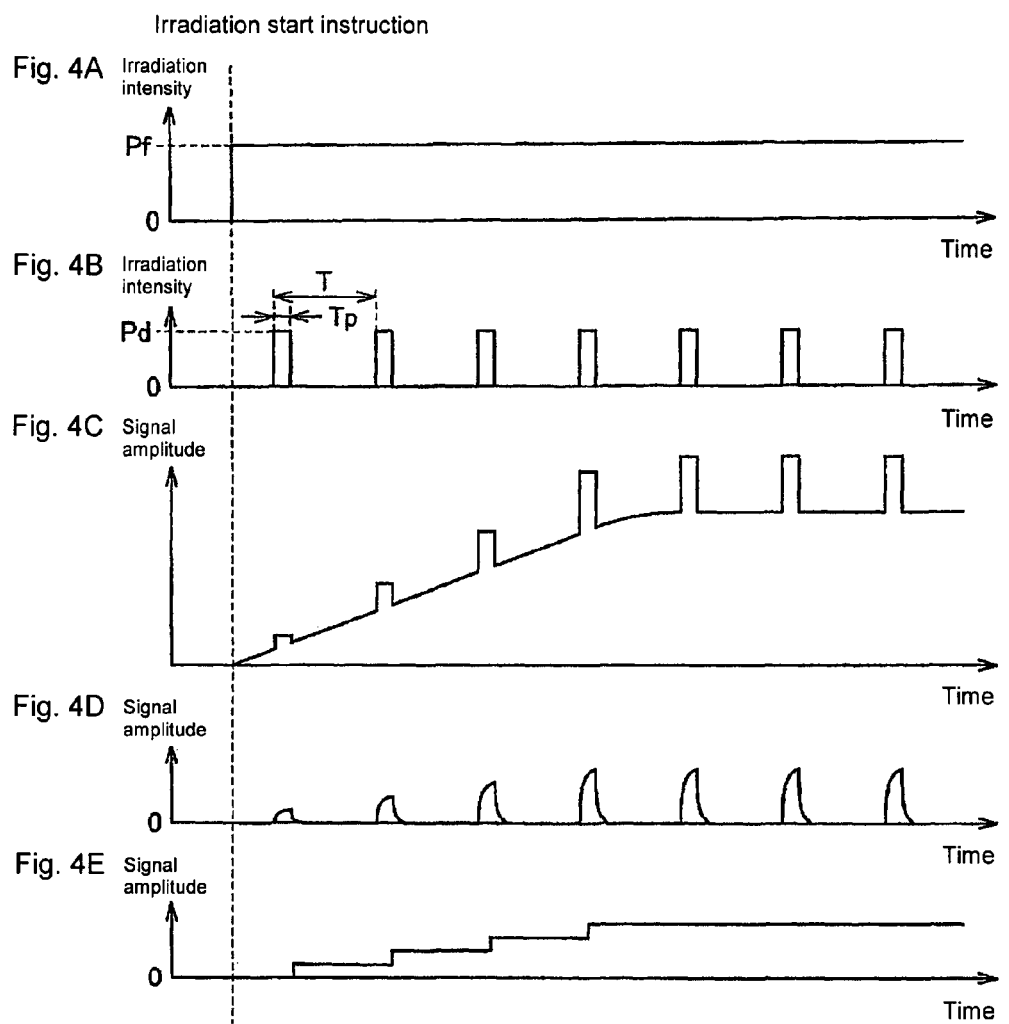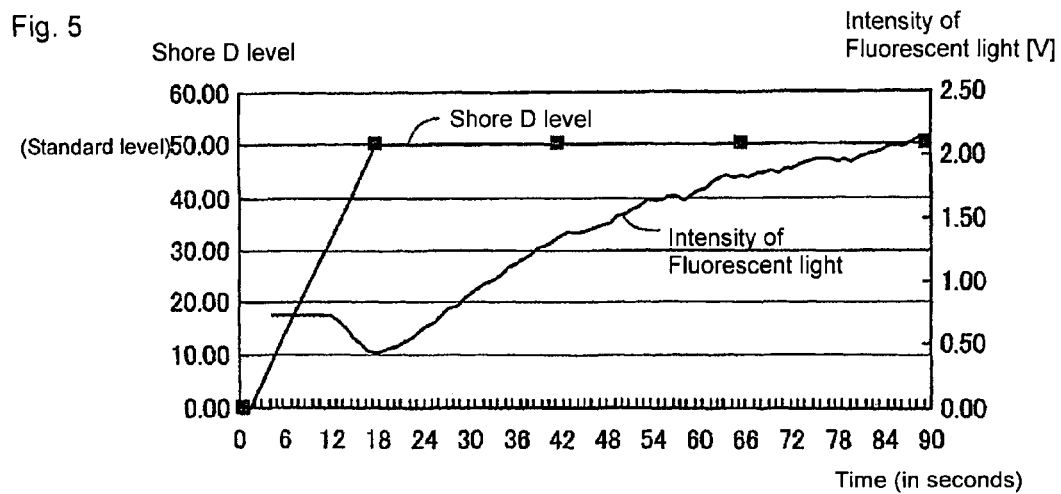

METHOD FOR ESTIMATING STATE OF ULTRAVIOLET CURING RESIN MATERIAL

This application claims priority from Japanese patent application P2006-071580, filed on Mar. 15, 2006. The entire contents of the aforementioned application is incorporated herein by reference.

FIELD OF THE INVENTION

The present invention relates to a method for estimating a state of an ultraviolet curing resin material which is cured when receiving an ultraviolet ray and particularly to a method for estimating a state of an ultraviolet curing resin material from a property of a photo polymerization initiator.

DESCRIPTION OF THE RELATED ART

In various industrial fields today, the ultraviolet curing method is used as a method for curing an adhesive or a coating agent. When compared with the thermal curing method using thermal energy, the ultraviolet curing method has many advantages such as emitting little amount of toxic substances to the atmosphere, minimizing the length of time required for curing, being applicable to highly heat-sensitive objects, and so on.

The ultraviolet curing method is based on ultraviolet curing resin materials which are usually in a liquid form before irradiation of an ultraviolet ray and turn into a solid form after the irradiation. Such an ultraviolet curing resin material includes a main agent selected from at least one of a monomer and an oligomer, and a photo polymerization initiator. The photo polymerization initiator when receiving an ultraviolet ray produces radicals and cations which then trigger a polymerizing action with the monomer or oligomer. As the polymerizing action proceeds, the monomer or oligomer turns into a polymer and its molecular weight significantly increases while its melting point falls. As a result, the ultraviolet curing resin material can no longer remain in a liquid form and turns into a solid form. Accordingly, in the ultraviolet curing method, the curing level of the ultraviolet curing resin material depends on the degree of polymerization.

It is, however, difficult to determine with visual observation the curing level or the level of quality of an ultraviolet curing resin material, and therefore a method enabling easy determination of a state of an ultraviolet curing resin material during the curing action (the polymerizing action) has been desired. Japanese Patent No. 2651036 discloses a method for monitoring the curing level of a curable coating material. The method includes a step of adding in an ultraviolet curable material a probe which contains a fluorescent component that emits a fluorescent light in such a way that it changes as a function of the degree of curing of the ultraviolet curable material, and measuring the light emission of the probe to determine the curing level of the ultraviolet curable material.

SUMMARY OF THE INVENTION

However, the method disclosed in Japanese Patent No. 2651036 of adding in an ultraviolet curing resin material a probe which emits a fluorescent light in such a way that it changes as a function of the curing level of the ultraviolet curable material is in many cases difficult to apply to a common ultraviolet curing process. More particularly, it is disadvantageous in terms of the cost to add a special material as the above-described probe, and addition of such a probe is sometimes unacceptable in view of the quality of the final product.

The present invention has been made for solving such problems and its object is to provide a method for easily estimating a state of an ultraviolet curing resin material, which is particularly applicable to a wide range of ultraviolet curing resin materials.

The inventors of the present invention discovered that, in response to irradiation of an ultraviolet ray, a photo polymerization initiator included in an ultraviolet curing resin material emits by itself an observable fluorescent light which is closely related to a state (e.g., the curing level) of the ultraviolet curing resin material, and has developed from the finding a novel method for easily estimating a state of an ultraviolet curing resin material.

The present invention provides a method for estimating a state of an ultraviolet curing resin material including a main agent selected from at least one of a monomer and an oligomer, and a photo polymerization initiator. The method includes an irradiating step of irradiating an ultraviolet ray to the ultraviolet curing resin material, a detecting step of detecting a fluorescent light emitted from the photo polymerization initiator when receiving the ultraviolet ray irradiated in the irradiating step, and an estimating step of estimating the state of the ultraviolet curing resin material based on the fluorescent light detected in the detecting step.

According to the present invention, an ultraviolet curing resin material is exposed to an ultraviolet ray for causing a fluorescent light, which is correlated with a state (e.g., the curing level) of the ultraviolet curing resin material, to be emitted from a photo polymerization initiator included in the ultraviolet curing resin material. The state of the ultraviolet curing resin material is estimated based on the fluorescent light emitted from the photo polymerization initiator. Therefore, a state of the ultraviolet curing resin material can be estimated without addition of a special material such as the probe in the prior art.

Preferably, the estimating step includes estimating the state of the ultraviolet curing resin material based on a change with time in intensity of the fluorescent light triggered by an curing action of the ultraviolet curing resin material during the irradiation of an ultraviolet ray for curing to cause the curing action of the ultraviolet curing resin material.

It is further preferred that the estimating step includes deciding that the photo polymerization initiator has substantially been consumed when the intensity of the fluorescent light after being increased is declined in an increasing speed, halted in the increase, or decreased.

It is further preferred that the estimating step includes deciding that the photo polymerization initiator has reached the maximum curing level when the intensity of the fluorescent light after being increased is declined in an increasing speed, halted in the increase, or decreased.

It is further preferred that the estimating step includes deciding that the ultraviolet curing resin material has reached a particular curing level when a difference or ratio between intensities of the fluorescent light before and after a start of increase exceeds a predetermined threshold.

It is further preferred that the estimating step includes deciding that the ultraviolet curing resin material has reached a particular curing level when the intensity of the fluorescent light exceeds a predetermined threshold.

It is further preferred that the estimating step includes estimating the state of the ultraviolet curing resin material by comparing the change with time in the detected intensity of the fluorescent light and a change with time predetermined as a reference value.

It is further preferred that the estimating step includes estimating the state of the ultraviolet curing resin material by obtaining duration of time from a particular reference time to occurrence of a particular change with time in the intensity of the fluorescent light, and comparing the obtained duration of time with a predetermined reference value.

It is also preferred that the estimating step includes estimating the state of the ultraviolet curing resin material based on intensity of the fluorescent light detected before the irradiation of the ultraviolet ray for curing to cause an curing action of the ultraviolet curing resin material.

It is also preferred that the estimating step includes estimating the state of the ultraviolet curing resin material based on intensity of the fluorescent light detected after the irradiation of the ultraviolet ray for curing to cause an curing action of the ultraviolet curing resin material.

It is also preferred that the estimating step includes estimating a state of structural stress accumulated in the ultraviolet curing resin material based on intensity of the fluorescent light detected in the ultraviolet curing resin material after realizing an curing action.

It is also preferred that the irradiating step includes irradiating an ultraviolet ray for detection to detect the fluorescent light emitted from the photo polymerization initiator and periodically being changed in intensity, and the detecting step includes a light receiving sub step of receiving a light emitted from the ultraviolet curing resin material, and an extracting sub step of extracting from the light received in the light receiving step, as the fluorescent light, a periodic component corresponding to a period of change in the intensity of the ultraviolet ray for detection.

It is further preferred that the ultraviolet ray for curing has substantially constant intensity with time, and the ultraviolet ray for detection is emitted in a predetermined period and has intensity of light in a pulse form.

According to the present invention, the method for easily estimating a state of an ultraviolet curing resin material, which is applicable to a wide range of ultraviolet curing resin materials, can be realized.

BRIEF DESCRIPTION OF THE DRAWINGS

FIGS. 4A-4E show diagrams of waveform profiles with time at different sections during detection of a fluorescent light;

FIG. 5 shows a diagram of the relation between the intensity of a fluorescent light and the curing level in Chemiseal U-1542 of Chemitech Inc.;

DETAILED DESCRIPTION OF THE PREFERRED EMBODIMENTS

Figure 1:
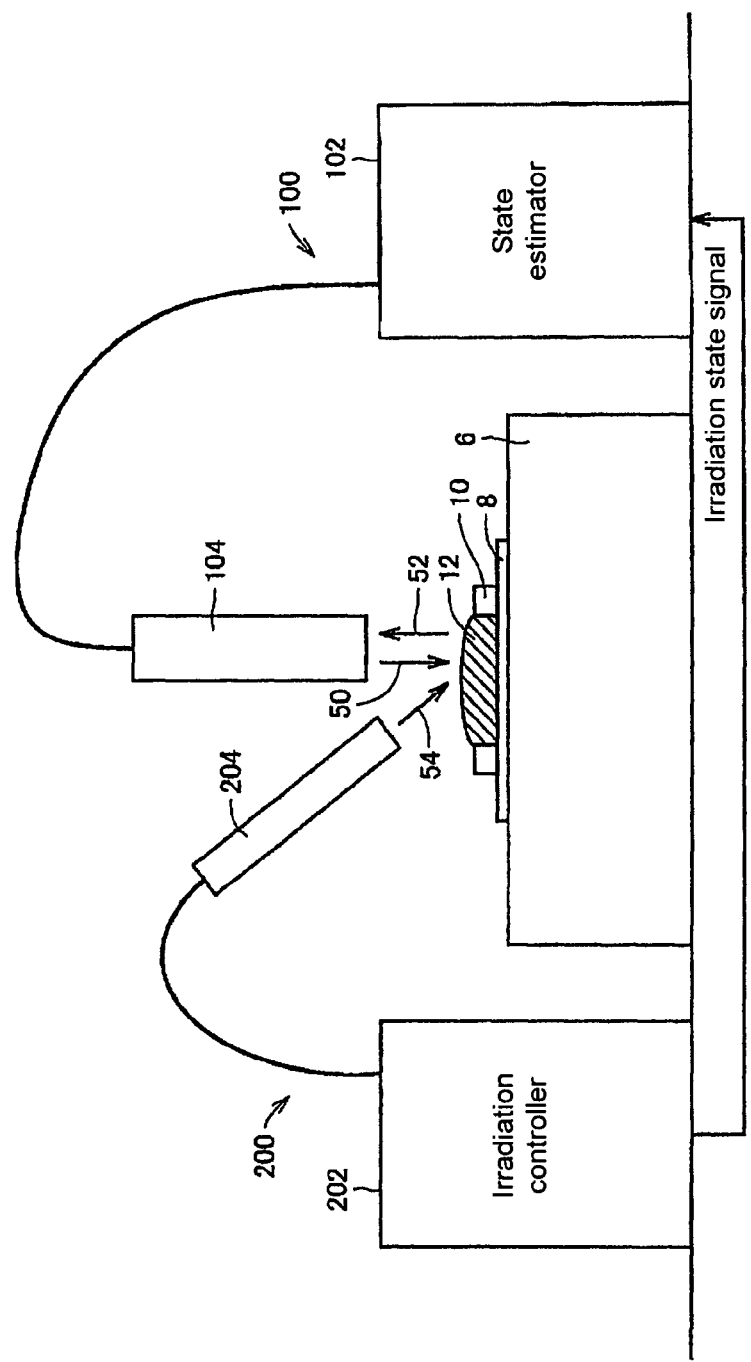
FIG. 1 shows a schematic illustration of one embodiment realizing a method for estimating a state of an ultraviolet curing resin material, according to the present invention.

One preferred embodiment according to the present invention will be described in more detail with reference to the drawings. The same or equivalent parts in the figures are denoted by the same reference numerals and their description will not be repeated.

The method for estimating a state of an ultraviolet curing resin material according to embodiments of the present invention is based on the phenomenon discovered by the inventors of the present invention, that a photo polymerization initiator included in the ultraviolet curing resin material emits by itself a fluorescent light which is closely related to a state (e.g., the curing level) of the ultraviolet curing resin material, in response to irradiation of an ultraviolet ray.

FIG. 1 shows a schematic view of an arrangement for realizing the method for estimating a state of an ultraviolet curing resin material according to an embodiment of the present invention.

Referring to FIG. 1, the method for estimating a state of an ultraviolet curing resin material according to an embodiment of the present invention estimates a state of an ultraviolet curing resin material 12 disposed on a specimen table 6 by using a state estimating apparatus 100 and a curing ultraviolet ray emitting apparatus 200. The state estimating apparatus 100 estimates a state of an ultraviolet curing resin material 12 of which curing action is triggered by irradiation of an ultraviolet ray for curing 54 from the curing ultraviolet ray emitting apparatus 200.

The state estimating apparatus 100 includes a fluorescent light detecting head 104 and a state estimator 102. When receiving an irradiation instruction from the state estimator 102, the fluorescent light detecting head 104 irradiates an ultraviolet ray for detection 50 on the ultraviolet curing resin material 12, receives a fluorescent light 52 emitted from the ultraviolet curing resin material 12, and outputs the detected intensity of the fluorescent light to the state estimator 102.

In response to an irradiation state signal from the curing ultraviolet ray emitting apparatus 200, the state estimator 102 gives an irradiation instruction to the fluorescent light detecting head 104. The state estimator 102 then estimates the state of the ultraviolet curing resin material 12 based on the intensity of the fluorescent light detected by the fluorescent light detecting head 104.

The curing ultraviolet ray emitting apparatus 200 includes an ultraviolet ray irradiating head 204 and an irradiation controller 202. When receiving an irradiation instruction from the irradiation controller 202, the ultraviolet ray irradiating head 204 generates and irradiates an ultraviolet ray for curing 54 for curing the ultraviolet curing resin material 12. When receiving an instruction from outside such as a user (not shown), the irradiation controller 202 transmits the irradiation instruction to the ultraviolet ray irradiating head 204, and in synchronization of the irradiation instruction, outputs an irradiation state signal to the state estimator 102.

The ultraviolet curing resin material 12 is injected into an annular member 10 disposed on a metal plate 8 and starts curing on receiving the ultraviolet ray for curing 54. The ultraviolet ray for curing 54 is irradiated so as to converge into a spot of substantially 14 mm in diameter on the ultraviolet curing resin material 12. In a series of experiments to be described later, the diameter of the ultraviolet curing resin material 12 (inner diameter of the annular member 10 shown in FIG. 3) is 7 mm, and the ultraviolet ray for curing 54 irradiates the entire ultraviolet curing resin material 12.

(Ultraviolet Curing Resin Material)

The ultraviolet curing resin material to be examined by the method according to the embodiments of the present invention is usually in a liquid form before irradiation of the ultraviolet ray for curing and turns into a solid form (by curing) after the irradiation. Throughout the description, the term "ultraviolet curing resin material" is comprehensively used for the liquid form before the irradiation of the ultraviolet ray and for the solid form after the irradiation of the ultraviolet ray.

The ultraviolet curing resin material before irradiation of an ultraviolet ray (prior to being cured) includes at least one of a monomer and an oligomer, a photo polymerization initiator, and other various additives. The monomer or oligomer is a main agent, and causes polymerizing action (e.g. chain bonding and bridging) with radicals and cations generated from the photo polymerization initiator when receiving an ultraviolet ray. The polymerizing action causes the monomer or oligomer to turn into a polymer, whereby the molecular weight significantly increases and the melting point falls. As a result, the ultraviolet curing resin material changes from a liquid form to a solid form.

The monomer and oligomer include, for example, polyester acrylate, urethane acrylate, polybutadiene acrylate, silicon acrylate, and epoxy acrylate. The monomer is also referred to as monomeric substance, which is a raw material for producing a polymer by polymerizing action. The oligomer is called a lower polymer whose degree of polymerization is relatively low as 2-20.

The photo polymerization initiator is generally classified into a radial polymerization initiator generating radicals when receiving an ultraviolet ray and a cation polymerization initiator generating cations when receiving an ultraviolet ray. The radical polymerization initiator is used for acrylic monomer or oligomer, and the cation polymerization initiator is used for epoxy or vinyl-ether monomer or oligomer. A photo polymerization initiator produced from a mixture of a radical polymerization initiator and a cation polymerization initiator has been put to practical use.

The radical polymerization initiator is classified into hydrogen abstraction type and intra-molecular cleavage type, depending on the generation process of radicals. The hydrogen abstraction type includes, for example, benzophenone and methyl ortho-benzoyl methyl benzoate. The intra-molecular cleavage type includes, for example, benzoin ether, benzyl-dimethyl-ketal, α-hydroxy-alkyl-phenone, α-amino-alkyl-phenone, methyl ortho-benzoyl-benzoate (OBM), 4-benzoyl-4'-methyl-diphenyl-sulfide (BMS), isopropyl-thio-xanthone (IPTX), diethyl-thio-xanthone (DETX), ethyl4-(diethylamino)-benzoate (DAB), 2-hydroxy-2-methyl-1-phenyl-propane-one, benzyl-dimethyl-ketal (BDK), and 1,2α-hydroxy-alkyl-phenone.

The cation polymerization includes, for example, diphenyl-iodonium salt. Throughout the description, the term "photo polymerization initiator" is used not only for an initiator capable of initiating photo polymerizing action but also for a substance which no longer contributes to initiation of photo polymerizing action due to, for example, a change caused by the photo polymerizing action of the initial photo polymerization initiator or to non-existence of the monomer or oligomer to be subjected to the photo polymerizing action. In many cases, the photo polymerization initiator after contributing to initiation of the photo polymerizing action is combined to an end of a polymer while generally maintaining the initial molecular size or being separated into two or more molecules. It is assumed that when the initial molecules of the photo polymerization initiator have been separated, at least portions of the molecules contribute to the emission of a fluorescent light.

(Emission of Fluorescent Light from Photo Polymerization Initiator)

Table 1 shows a result of examining the emission of the fluorescent light of some known types of the ultraviolet curing resin material. As shown in Table 1, the emission of the fluorescent light is expressed in the form of peak wavelength when the ultraviolet ray having the wavelength of 365 nm irradiates each of 22 kinds of the ultraviolet curing resin materials, using a spectrum analyzer.

TABLE 1

| Photo polymerization initiators | Emission of fluorescent light | Peak wavelength |
|---|---|---|
| ThreeBond 3034 | ◯: Emitted | 420 nm |
| ThreeBond 3114 | ◯: Emitted | 470 nm |
| ThreeBond 3033 | ◯: Emitted | 450 nm |
| ThreeBond 3042 | ◯: Emitted | 460 nm |
| ThreeBond 3065 | ◯: Emitted | 480 nm |
| ThreeBond 3064 | ◯: Emitted | 500 nm |
| ThreeBond 3113B | ◯: Emitted | 420 nm 500 nm |
| ThreeBond 3114B | ◯: Emitted | 480 nm |
| ThreeBond 3056B | ◯: Emitted | 420 nm 530 nm |
| Three-bond 3134 | ◯: Emitted | 470 nm |
| Chemi-seal U-1582 by ChemiTech Inc. | ◯: Emitted | 480 nm |
| Chemi-seal U-1481 by ChemiTech Inc. | ◯: Emitted | 430 nm |
| Chemi-seal U-1595 by ChemiTech Inc. | ◯: Emitted | 420 nm |
| Chemi-seal U-406B by ChemiTech Inc. | ◯: Emitted | 470 nm |
| Chemi-seal U-1541 by ChemiTech Inc. | ◯: Emitted | 420 nm 520 nm |
| Chemi-seal U-1542 by ChemiTech Inc. | ◯: Emitted | 480 nm |
| Chemi-seal U-1542J by ChemiTech Inc. | ◯: Emitted | 470 nm |
| Chemi-seal U-403B by ChemiTech Inc. | ◯: Emitted | 480 nm |
| Chemi-seal U-1455B by ChemiTech Inc. | ◯: Emitted | 430 nm |
| Chemi-seal U-1537 by ChemiTech Inc. | ◯: Emitted | 425 nm 510 nm |
| Chemi-seal U-483B by ChemiTech Inc. | ◯: Emitted | 470 nm |
| Chemi-seal U-401 by ChemiTech Inc. | ◯: Emitted | 420 nm 500 nm |

It is apparent from Table 1 that all the samples of the ultraviolet curing resin material emit fluorescent light of longer wavelengths than that of the irradiated ultraviolet ray (365 nm of the wavelength).

The ultraviolet curing resin material is arranged to be cured by the polymerizing action when receiving an ultraviolet ray. Because of this, the photo polymerization initiator has characteristics such as: (1) being highly capable of generating active species (radicals and acids) for initiating the polymerizing action (quantum yield and molar absorption coefficient), (2) generating highly reactive species, and (3) having the spectrum range of excitation energy in an ultraviolet range for encouraging the generation of active species. More particularly, the photo polymerization initiator preferably has such a molecular structure that is high in the absorption of the ultraviolet ray and favorable for transferring the energy (of electrons) generated by the absorption of ultraviolet ray to other molecules.

The monomer or oligomer as a main agent in the ultraviolet curing resin material has substantially no function of emitting the fluorescent light. The structure of the monomer or oligomer has a structure that disallows carriers (electrons) to freely travel in molecules.

As described above, the inventors of the present invention have concluded that the photo polymerization initiator inherently has a property of emitting a fluorescent light when receiving an ultraviolet ray.

However, as far as the inventors know, there is no prior art which discloses the realization that the photo polymerization initiator emits a fluorescent light. The reason behind this fact may be as follows.

Although it is true that the photo polymerization initiator is theoretically capable of emitting a fluorescent light, the intensity of the emitted fluorescent light is too weak to be perceived by human eyes. On the contrary, the fluorescent light emitted from any known fluorescent material can easily be perceived by human eyes. The attempt described in the foregoing prior art for estimating the curing level from the fluorescent light emitted from a probe is hence based on the conception of adding a material which can emit a fluorescent light of significant intensity.

Also, in addition to the fact that the intensity of the fluorescent light emitted from the photo polymerization initiator is too weak, the ultraviolet curing resin material requires detection of the intensity of the fluorescent light to be carried out during the irradiation of a strong ultraviolet ray for curing the resin material. It is hence needed for ensuring the detection of the fluorescent light to devise ways of measuring, for example, separating the fluorescent light by means of a wavelength filter, irradiating a pulse form of the ultraviolet ray for detection of the fluorescent light other than the ultraviolet ray for curing, and detecting the emission of fluorescent light in synchronization. Moreover, before ultraviolet light emitting diodes (LED) become commercially available, ultraviolet lamps were almost the only source of emitting the ultraviolet ray, with which it was difficult to emit the ultraviolet ray in a pulse form.

(Measurement of Fluorescent Light)

Figure 2:
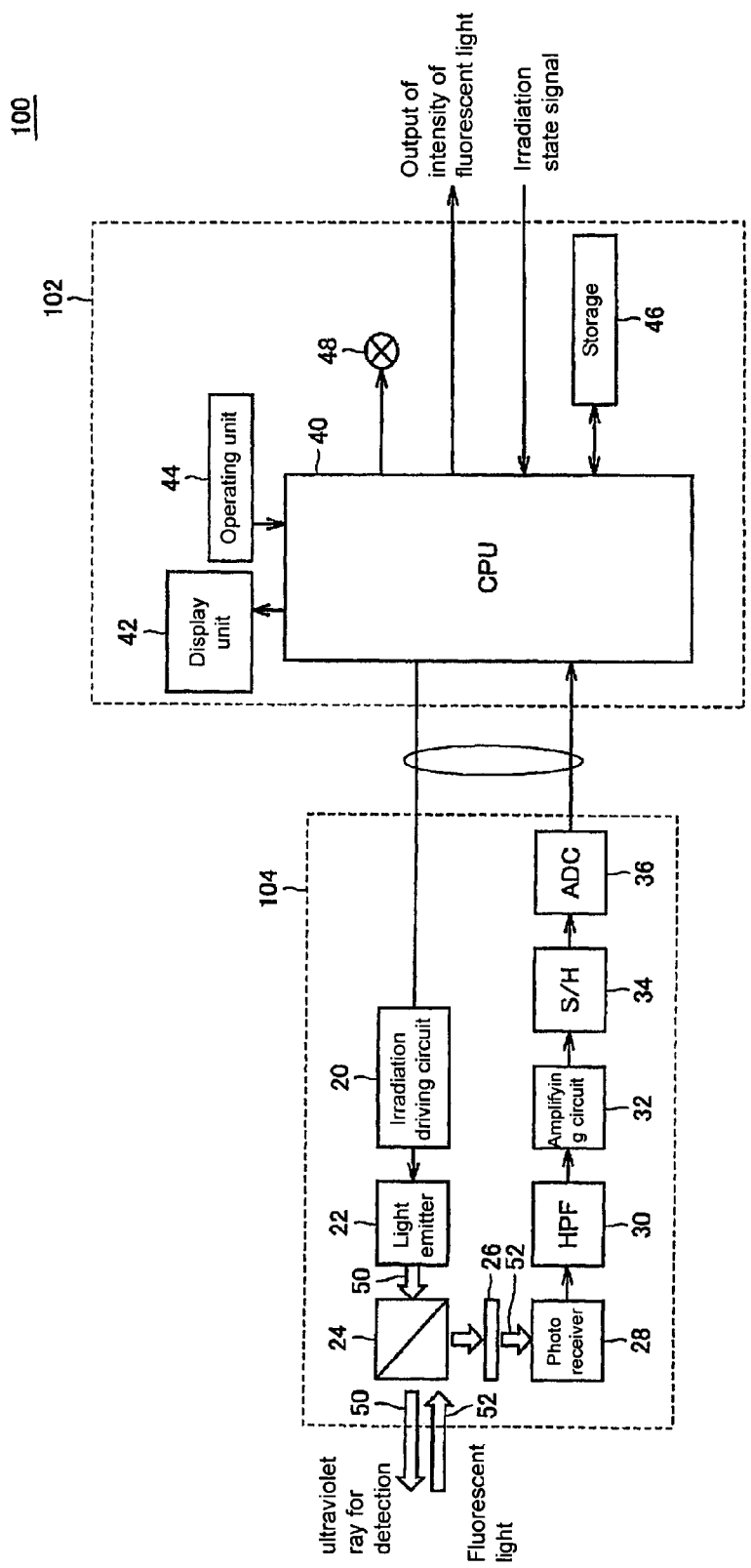
FIG. 2 shows a block diagram of a state estimating system in more detail.

FIG. 2 is a block diagram showing the state estimating apparatus 100 in more detail.

As shown in FIG. 2, the state estimator 102 includes a CPU (central processing unit) 40, a display unit 42, an operating unit 44, a storage unit 46, and an irradiation warning unit 48.

The CPU 40 when receiving an operation instruction from the operating unit 44 and an irradiation state signal from the curing ultraviolet ray emitting apparatus 200 (FIG. 1) outputs an irradiation instruction to the fluorescent light detecting head 104. Also, as timed with the irradiation instruction to the fluorescent light detecting head 104, the CPU 40 directs the irradiation warning unit 48 to start an illuminating action or a flashing action for releasing a signal of protecting from the ultraviolet ray for detection 50 emitted from the fluorescent light detecting head 104. The CPU 40 then examines the intensity of the fluorescent light detected by the fluorescent light detecting head 104, estimates a state of the ultraviolet curing resin material to be monitored, and outputs the result of the estimation to the display unit 42. Simultaneously, the CPU 40 outputs a signal (in analog or digital form) indicating the intensity of the fluorescent light detected by the fluorescent light detecting head 104 to an external apparatus (not shown). The CPU 40 reads out a variety of data from the storage unit 46 and stores data of the measurement in the storage unit 46.

The display unit 42 includes a display such as a LCD (liquid crystal display) or a CRT (cathode-ray tube) for displaying the data sent from the CPU 40 such as of changes in the intensity of fluorescent light in, e.g., graphic representations.

The operating unit 44 includes various switches which are operated by the user, and outputs operation instructions corresponding to the operation to the CPU 40.

The irradiation warning unit 48 includes, for example, an LED or a lamp for notifying the user or worker near the state estimating apparatus 100 of the irradiation of ultraviolet ray.

The storage unit 46 includes, for example, an EEPROM (electrically erasable and programmable read-only-memory) which stores data of the measurement and a variety of data associated with types of the ultraviolet curing resin material.

The fluorescent light detecting head 104 includes an irradiation driving circuit 20, a light emitter 22, a half mirror 24, an optical filer 26, a photo receiver 28, a high pass filer (HPF) 30, an amplifying circuit 32, a sample and hold (S/H) circuit 34, and an analog/digital converter (ADC) 36.

The irradiation driving circuit 20 when receiving the irradiation instruction from the CPU 40 supplies the light emitter 22 with pulses of voltage at predetermined intervals.

The light emitter 22 may be an ultraviolet LED for generating and emitting the ultraviolet ray for detection 50 in response to the pulses of voltage applied by the irradiation driving circuit 20. In this embodiment, the ultraviolet ray for detection 50 emitted from the light emitter 22 has a wavelength of 365 nm at the peak value.

The half mirror 24 is disposed on an optical axis as coaxial with the light emitter 22. The half mirror 24 allows the ultraviolet ray for detection 50 emitted from the light emitter 22 to pass through and the fluorescent light 52 emitted from the ultraviolet curing resin material (not shown) to be examined to deflect and run to the optical filter 26. Preferably, the half mirror 24 has its reflection surface finished by a metal vapor deposition technique.

The optical filter 26 is disposed to remove any external interrupting lights including the ultraviolet ray for detection 50 emitted from the light emitter 22. Its installation is so determined that an ultraviolet range of the light is attenuated while a visible range of the light is passed through. In this embodiment, the optical filter 26 is a multi-layer dielectric film which can pass a component of the light at a wavelength of not lower than 410 nm.

The light emitter 28 includes, for example, a photo diode for generating an electric current corresponding to the intensity of the fluorescent light which enters after passing through the optical filter 26 and outputting the same to the HPF 30.

The HPF 30 then removes direct current components and low frequency components from the fluorescent light intensity signal received from the light emitter 28 and passes a predetermined component which is on or above a particular frequency of the signal thus to extract the ultraviolet ray for detection 50.

The amplifying circuit 32 amplifies the predetermined component of the signal passed through the HPF 30 at a given amplifying rate (a current/voltage convertion rate) before outputting the same to the S/H circuit 34.

The S/H circuit 34, in synchronization with the emission of light from the light emitter 22, samples the received light intensity signal and holds its sampled value until the subsequent sampling is conducted, thus detecting and saving the maximum of amplitude at each interval in the signal where the ultraviolet ray in a pulse form is irradiated.

The analog/digital converter 36 converts a voltage signal (analog signal) outputted from the S/H circuit 34 into a digital form which, and outputs the same to the CPU 40.

Figure 3:
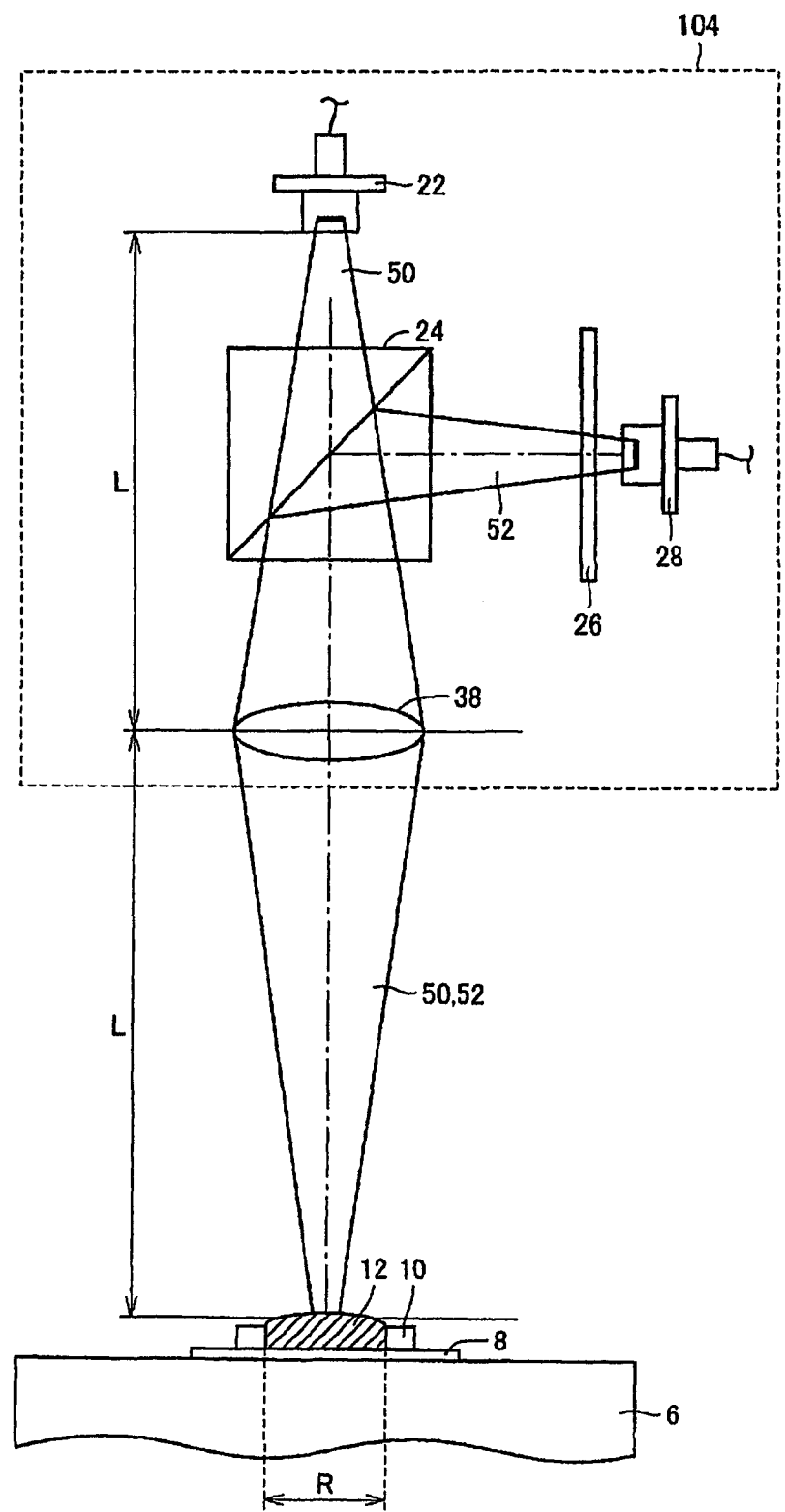
FIG. 3 shows a schematic view of an optical system in a fluorescent light detecting head.

FIG. 3 is a schematic view showing an optical system in the fluorescent light detecting head 104.

As shown in FIG. 3, the fluorescent light detecting head 104 further includes a convergence lens 38. With the light emitter 22, the half mirror 24, the convergence lens 38, and the ultraviolet curing resin material 12 to be examined linearly aligned, the ultraviolet ray for detection 50 emitted from the light emitter 22 is focused by the convergence lens 38 onto the spot of substantially 7 mm in the diameter on the ultraviolet curing resin material 12. Since the diameter of the ultraviolet curing resin material 12 (in the annular member 10 shown in FIG. 3) is 7 mm throughout a series of experiments to be described below, the ultraviolet ray for detection 50 falls entirely on the ultraviolet curing resin material 12. The fluorescent light 52 emitted from the ultraviolet curing resin material 12 propagates in a reverse direction of the ultraviolet ray for detection 50 and then reflects on the half mirror 24. The fluorescent light 52 enters through the optical filter 26 in the photo receiver 28.

The distance between the emitting surface of the light emitter 22 and the convergence lens 38 is set substantially identical to the distance from the convergence lens 38 to the ultraviolet curing resin material 12.

As the fluorescent light 52 emitted from the fluorescent curing resin material 12 is reflected by the half mirror 24, it is definitely separated from the ultraviolet ray for detection 50 which runs along the same optical axis and can thus be detected at high accuracy even if its intensity is low.

Referring again to FIG. 1, as the photo polymerization initiator included in the ultraviolet curing resin material 12 emits a fluorescent light when receiving an ultraviolet ray, it emits a fluorescent light when receiving the ultraviolet ray for curing. More specifically, the photo polymerization initiator emits the fluorescent light equally when receiving either the ultraviolet ray for curing 54 or the ultraviolet ray for detection 50.

The state estimating apparatus 100 according to the embodiment of the present invention is hence arranged to emit the ultraviolet ray for detection 50 which changes periodically in the intensity and detect the fluorescent light emitted from the photo polymerization initiator. When the surrounding environment of the ultraviolet curing resin material 12 is illuminated by an ambient light including the same wavelength band as that of the fluorescent light emitted from the ultraviolet curing resin material 12, the ambient light is an external interrupting light. As the ambient light in the environment is varied throughout a range of frequencies of the commercial power source, the period of change in the intensity of the ultraviolet ray for detection 50 is set to be shorter than that of the ambient light. In common, the ultraviolet ray for detection 54 is irradiated at a direct current mode without any change in the intensity. In the case where the ultraviolet ray for curing 54 is varied periodically in the intensity, the period of change in the intensity of the ultraviolet ray for detection 50 is set to a length different from that of the ultraviolet ray for curing 54 (for example, as shorter than the period of change in the intensity of the ultraviolet ray for curing 54). More specifically, the state estimating apparatus 100 is arranged to emit the ultraviolet ray for detection 50 which is separable by frequencies from both the ambient light and the ultraviolet ray for curing 54. Hence, the apparatus 100 detects the fluorescent light of weak intensity and estimates a state of the ultraviolet curing resin material 12.

For instance, the state estimating apparatus 100 according to the embodiment of the present invention emits an ultraviolet ray for detection 50 in a pulse form periodically. On the other hand, the curing ultraviolet ray emitting apparatus 200 emits the ultraviolet ray for curing 54 has substantially constant intensity with time. The HPF 30 in the fluorescent light detecting head 104 removes direct current components and low frequency components from the light which is received by the photo receiver 28 and changes in the intensity, thus to extract, as the fluorescent light, a periodic component corresponding to a period of change in the intensity (a pulse emission period) of the ultraviolet ray for detection 50.

FIG. 4 is a schematic diagram showing waveform profiles with time measured at different sections for detecting the fluorescent light.

FIG. 4A is a waveform profile with time of the ultraviolet ray for curing 54 emitted from the ultraviolet ray irradiating head 204.

FIG. 4B is a waveform profile with time of the ultraviolet ray for detection 50 emitted from the fluorescent light detecting head 104.

FIG. 4C is a waveform profile with time of the intensity of the light received by the photo receiver 28.

FIG. 4D is a waveform profile with time of the signal outputted from the HPF 30.

FIG. 4E is a waveform profile with time of the signal outputted from the S/H circuit 34.

As shown in FIG. 4A, the irradiation controller 202, upon receiving an irradiation start instruction from the user, starts emission of the ultraviolet ray for curing 54 with a particular intensity from the ultraviolet ray irradiating head 204. In the embodiment of the present invention, the ultraviolet ray irradiating head 204 is arranged to emit the ultraviolet ray for curing 54 which is 365 nm in wavelength and Pf=20 mW in intensity. This will remain unchanged throughout the description.

As shown in FIG. 4B, the state estimator 102, when receiving an irradiation state signal indicative of the start of emission of the ultraviolet ray for curing 54 from the irradiation controller 202, starts emission in predetermined periods of the ultraviolet ray for detection 50 whose intensity changes in a pulse form from the fluorescent light detecting head 104. In the embodiment of the present invention, the fluorescent light detecting head 104 is arranged to emit the ultraviolet ray for detection 50 in a pulse form in periods of T=0.35 ms which is 365 nm in wavelength, Pd=12 mW at peak intensity, and Tp=18 μs in pulse width. This will be unchanged throughout the description.

As shown in FIG. 4C, the fluorescent light emitted from the photo polymerization initiator is closely related with a state (e.g., the curing level) of the ultraviolet curing resin material 12. As the curing level of the ultraviolet curing resin material 12 changes with the irradiation of the ultraviolet ray for curing 54, the intensity of the fluorescent light emitted from the photo polymerization initiator changes. The ultraviolet curing resin material 12 is irradiated by both the ultraviolet ray for curing 54 (FIG. 4A) which has constant intensity and the ultraviolet ray for detection 50 (FIG. 4B) which is changed in pulses in the intensity, as described previously. The intensity of the light received by the photo receiver 28 hence has the waveform with time of a composite light including the fluorescent light emitted upon receiving the ultraviolet ray for curing 54 and the ultraviolet ray for detection 50.

As shown in FIG. 4D, the signal of the intensity of the received light is outputted from the photo receiver 28 to the HPF 30 where the component generated by the ultraviolet ray for detection 50 is extracted. In other words, the HPF 30 functions as a differentiator to extract a component corresponding to the pulse component of the ultraviolet ray for detection 50.

As shown in FIG. 4E, the signal of the intensity of the received light from the HPF 30 is received by the S/H circuit 34 which detects and holds the maximum amplitude in each irradiation period of the ultraviolet ray for detection 50. The signal of the intensity of the received light which carries the intensity of the fluorescent light emitted from the photo polymerization initiator is then outputted from the S/H circuit 34 to the state estimator 102.

As explained, the state estimating apparatus 100 emits the ultraviolet ray for detection 50 which is separable by frequencies from the ambient light in the environment and the ultraviolet ray for curing 54, and can thus detect the fluorescent light of a very low intensity at favorable accuracy while eliminating the influence of the ambient light or external interrupting light and of the unwanted fluorescent light generated by the ultraviolet ray for curing 54.

Although FIG. 4 illustrates the case where the time required for curing the ultraviolet curing resin material 12 is set to a shorter length than the period of emission of the ultraviolet ray for detection 50 for understandability, the time required for curing the ultraviolet curing resin material 12 (e.g., some seconds to some tens seconds) is usually very long when compared with the period of emission of the ultraviolet ray for detection 50 (0.35 ms). Accordingly, as the ultraviolet curing resin material 12 receives the ultraviolet ray for detection 50 for a period much longer than the time for curing, the fluorescent light emitted can be detected with high accuracy.

The CPU 40 (FIG. 2) in the state estimator 102 is arranged to calculate the intensity of the fluorescent light emitted from the photo polymerization initiator by performing a moving average process of the measurements of the intensity of the fluorescent light received via the analog/digital converter 36 from the S/H circuit 34. In the embodiment of the present invention, the CPU 40 performs a moving average process over 256 pieces of the data (0.35 ms×256=89.6 ms). This will remain unchanged throughout the description.

(Result of Measurements)

Using the state estimating apparatus 100, a change in the intensity of the fluorescent light from (five samples of) the commercially available ultraviolet curing resin material was measured. At the same time, the curing level of the ultraviolet curing resin material was measured during the curing action.

FIG. 5 illustrates a profile of the relation between the intensity of fluorescent light and the curing level of the sample of Chemiseal U-1542 by Chemitech Inc.

Figure 6:
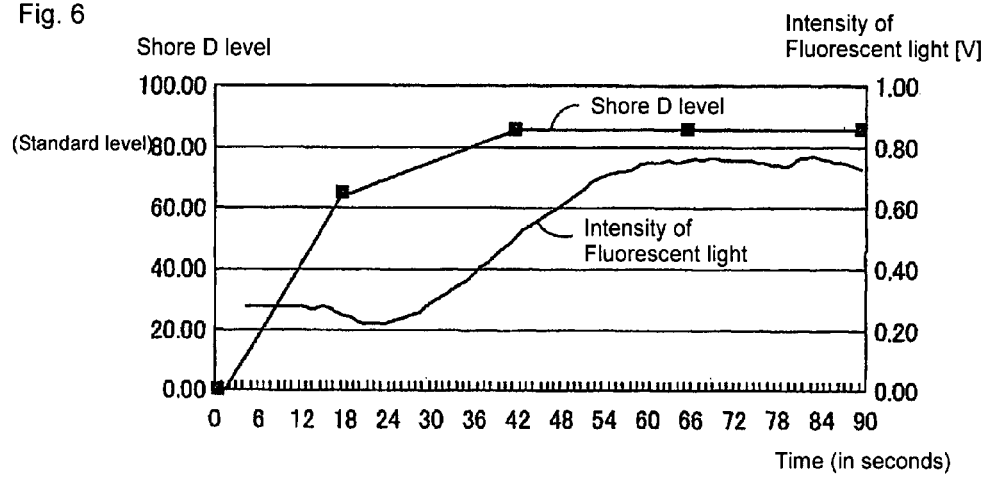
FIG. 6 shows a diagram of the relation between the intensity of a fluorescent light and the curing level in Chemiseal U-406B of Chemitech Inc.

FIG. 6 illustrates a profile of the relation between the intensity of fluorescent light and the curing level of the sample of Chemiseal U-40B by Chemitech Inc.

Figure 7:
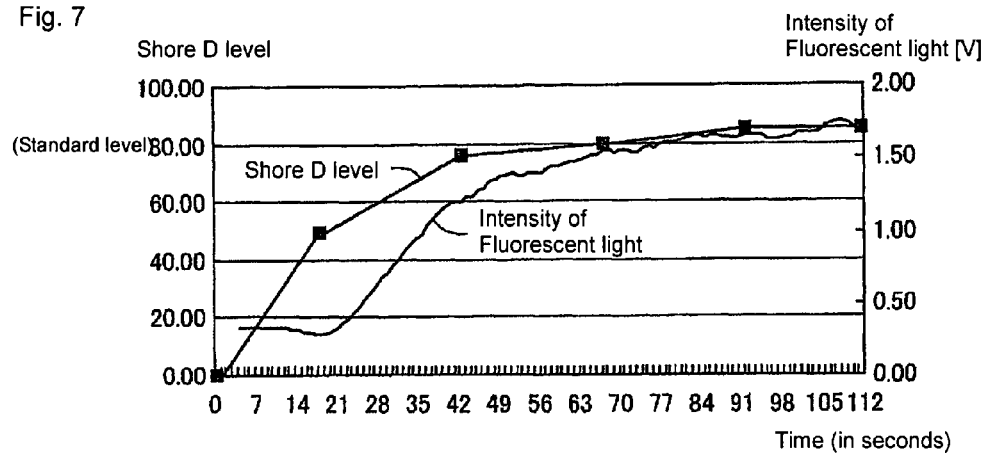
FIG. 7 shows a diagram of the relation between the intensity of a fluorescent light and the curing level in Chemiseal U-1481 of Chemitech Inc.

FIG. 7 illustrates a profile of the relation between the intensity of fluorescent light and the curing level of the sample of Chemiseal U-1481 by Chemitech Inc.

Figure 8:
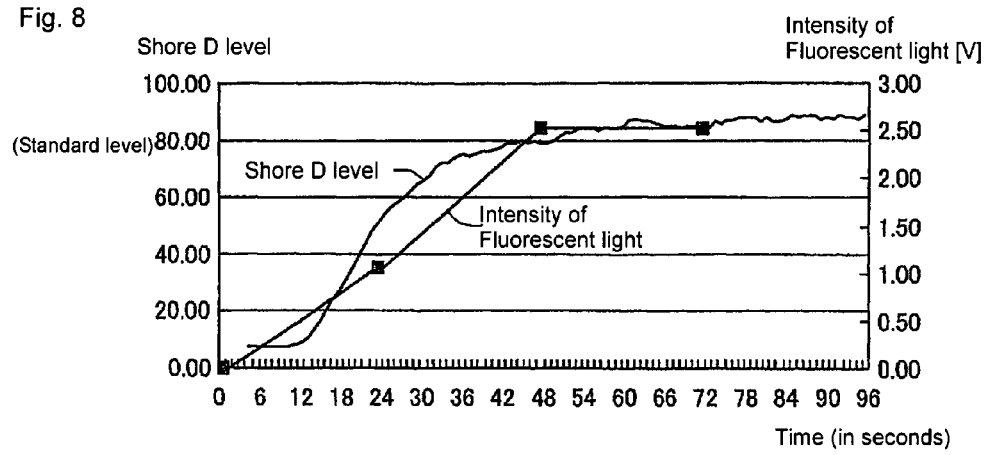
FIG. 8 shows a diagram of the relation between the intensity of a fluorescent light and the curing level in ThreeBond 3065 of ThreeBond Co., Ltd.

FIG. 8 illustrates a profile of the relation between the intensity of fluorescent light and the curing level of the sample of 3065 by ThreeBond Co., Ltd.

Figure 9:
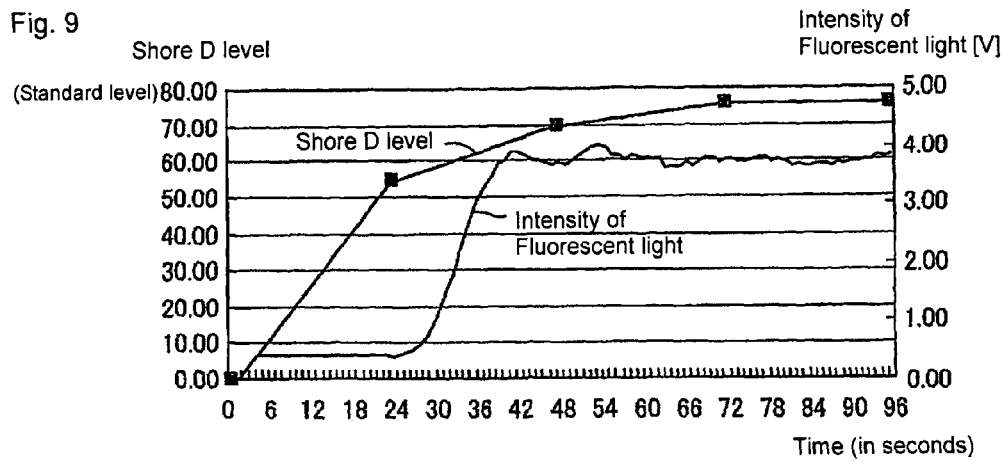
FIG. 9 shows a diagram of the relation between the intensity of a fluorescent light and the curing level in ThreeBond 3114B of ThreeBond Co., Ltd.

FIG. 9 illustrates a profile of the relation between the intensity of fluorescent light and the curing level of the sample of 3114B by ThreeBond Co., Ltd.

Throughout FIGS. 5 to 9, the curing level of the samples of the ultraviolet curing resin material was measured by a measuring method conforming to JIS K7215. The curing level is expressed in Shore D notation. Since the polymerizing action continuously proceeds due to the characteristic of the ultraviolet ray curing technique even when the irradiation of the ultraviolet ray is canceled during the curing action, the measurement on each sample cannot be repeated at different points of time. For compensation, a group of the same samples was irradiated by the ultraviolet ray for curing 54 under the same conditions, and one of them was picked out at each measuring point of time for measuring the curing level.

The amplifying rate (current/voltage converting rate) in the amplifying circuit 32 shown in FIG. 2 is 0.18 V/μA, and the intensity of the fluorescent light outputted from the fluorescent light detecting head 104 and the power of the received fluorescent light are expressed by 250 nW/1V.

Shown in FIG. 5 is a sample of the ultraviolet curing resin material of Chemiseal U-1542 by Chemitech Inc. at 50 of Shore D (as standardized in its catalog). The standardized value represents the maximum of the curing degree of the ultraviolet curing resin material reached under predetermined conditions. In some cases, the curing level may exceed or may not reach the standardized value depending on the intensity or the duration of irradiation of the ultraviolet ray for curing 54.

As illustrated, the Shore D level of the ultraviolet curing resin material reached the standardized value about 20 seconds after the start of the irradiation. The intensity of the fluorescent light temporarily declined about 20 seconds after the start of the irradiation and then increased gradually and continuously.

Shown in FIG. 6 is a sample of the ultraviolet curing resin material of Chemiseal U-406B by Chemitech Inc. at 80 of Shore D (as standardized in its catalog). The Shore D level of this ultraviolet curing resin material reached the standardized value about 40 seconds after the start of the irradiation. The intensity of the fluorescent light temporarily declined about 25 seconds after the start of the irradiation and then increased gradually. The speed of its increase fell down about 70 seconds after the start of the irradiation.

Shown in FIG. 7 is a sample of the ultraviolet curing resin material of Chemiseal U-1481 by Chemitech Inc. at 80 of Shore D (as standardized in its catalog). The Shore D level of this ultraviolet curing resin material reached the standardized value about 90 seconds after the start of the irradiation. The intensity of the fluorescent light slightly declined just after the start of the irradiation and then increased gradually about 20 seconds after the start of the irradiation. The speed of its increase fell down about 90 seconds after the start of the irradiation.

Shown in FIG. 8 is a sample of the ultraviolet curing resin material of 3065 by ThreeBond Co., Ltd. at 80 of Shore D (as standardized in its catalog). The Shore D level of this ultraviolet curing resin material reached the standardized value about 50 seconds after the start of the irradiation. The intensity of the fluorescent light increased about 15 seconds after the start of the irradiation. The speed of its increase fell down about 40 seconds after the start of the irradiation and the increase substantially stopped about 60 seconds after the start of the irradiation.

Shown in FIG. 9 is a sample of the ultraviolet curing resin material of 3114B by ThreeBond Co., Ltd. at 80 of Shore D (as standardized in its catalog). The Shore D level of this ultraviolet curing resin material reached the standardized value about 70 seconds after the start of the irradiation. The intensity of the fluorescent light increased about 30 seconds after the start of the irradiation and its increase stopped about 40 seconds after the start of the irradiation.

As shown in FIGS. 5 to 9, in the fluorescent light emitted during the irradiation of the ultraviolet curing resin material by the ultraviolet ray for curing 54 for the curing action, its intensity fundamentally increases even when, in some cases, having been declined temporarily. This may be explained from the following reason.

As the curing action (the polymerizing action) proceeds, the photo polymerization initiator is consumed (i.e., its non-reacted portion decreases), a portion of the light energy generated by absorption of the ultraviolet ray to be used as a chemical energy for generating the active species (radicals and acids) also decreases. Meanwhile, as the photo polymerization initiator maintains its property of absorbing the ultraviolet ray even after the polymerizing action, the light energy generated by absorption of the ultraviolet ray does not decrease and can be turned into another form of energy, such as fluorescent light or heat, which is different from the chemical energy. This allows the intensity of the fluorescent light to increase as the curing action of the ultraviolet curing resin material proceeds. This tendency is pertinent to the basic composition of the ultraviolet curing resin material and can thus be commonly observed in almost all types of the ultraviolet curing resin material.

Figure 10:
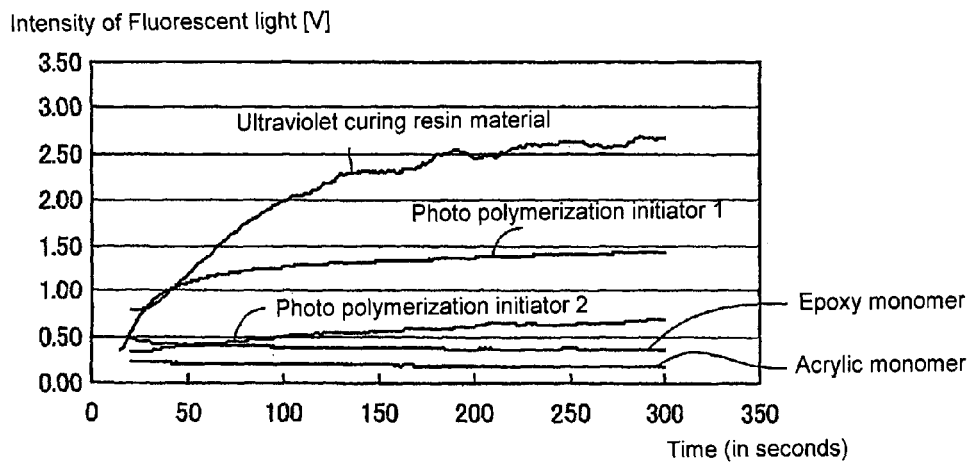
FIG. 10 shows a waveform profile with time of individual components of an ultraviolet curing resin material.

FIG. 10 illustrates a waveform profile with time of the intensity of the fluorescent light for individual different compositions of the ultraviolet curing resin material. Shown in FIG. 10 are measurements of the intensity of the fluorescent light emitted from each of the different compositions of the ultraviolet curing resin material, which are a photo polymerization initiator 1, a photo polymerization initiator 2, an acrylic monomer, and an epoxy monomer, when irradiated by the ultraviolet ray for curing 54. Also, a waveform profile with time of the intensity of the fluorescent light emitted from the ultraviolet curing resin material is shown in FIG. 10.

In one example, the ultraviolet curing resin material is ThreeBond 3065, the photo polymerization initiator 1 is Igracure 369 (registered trademark) of Ciba Specialty Chemicals 2-benzyl-2-dimethyl-1-(4-morpholino-phenyl)-butanone-1), and the photo polymerization initiator 2 is Igracure 184 (registered trademark) of Ciba Specialty Chemicals (1-hydroxy-cyclohexyl-phenyl-ketone). The epoxy monomer is substituted with 4,4-isopropylidene-diphenol (bisphenol A). It should be noted that the photo polymerization initiator 1, the photo polymerization initiator 2, the acrylic monomer, and the epoxy monomer are not always included in the ultraviolet curing resin material (of ThreeBond 3065).

As apparent from FIG. 10 similar to FIG. 8, the intensity of the fluorescent light from the ultraviolet curing resin material increased as the curing action proceeds. While the ultraviolet curing resin material shown in FIG. 10 is identical with that shown in FIG. 8, its waveform profile appears slightly different due to a difference in the measuring conditions (including the temperature).

Both the photo polymerization initiators 1 and 2 are similar in the intensity change of the fluorescent light during the irradiation of the ultraviolet ray for curing 54, and have a common tendency with the intensity change of the fluorescent light emitted from the ultraviolet curing resin material. The absolute value of the intensity of the fluorescent light from both the photo polymerization initiators 1 and 2 is smaller than, but not greatly smaller than, the absolute value of the intensity of the fluorescent light from the ultraviolet curing resin material. It is thus consistent with the assumption that the fluorescent light emitted from the ultraviolet curing resin material is from the photo polymerization initiator. It is also found through the experiments that the photo polymerization initiator possibly emits the fluorescent light of a smaller intensity with no presence of the monomer or oligomer, which is subjected to the polymerizing action, than when it is added in the ultraviolet curing resin material.

The fluorescent light emitted either from the acrylic monomer or the epoxy monomer during the irradiation of the ultraviolet ray for curing 54 does not increase in the intensity. The absolute value of the intensity of the fluorescent light emitted either from the acrylic monomer or the epoxy monomer is smaller than that of the intensity of the fluorescent light emitted either from the ultraviolet curing resin material or the photo polymerization initiator.

It is hence apparent from the measurements shown in FIG. 10 that only the photo polymerization initiators 1 and 2 are the material emitting the fluorescent light which is increased with time in the intensity as the ultraviolet curing resin material.

Figure 11:
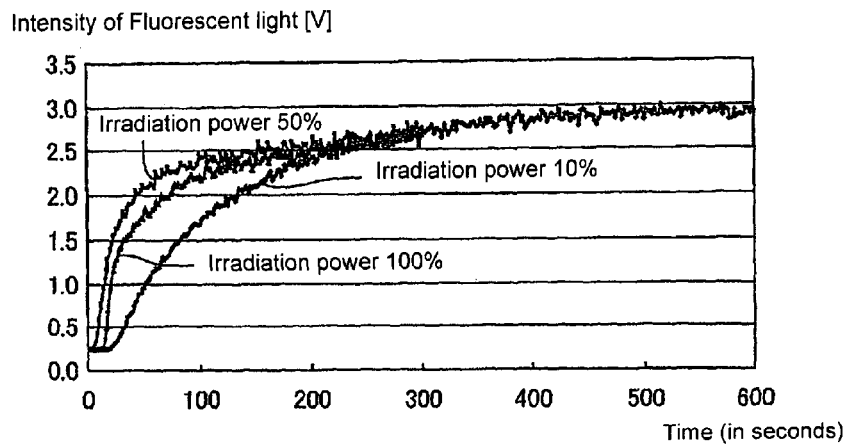
FIG. 11 shows a diagram of the relation between the irradiation power of an ultraviolet ray for curing and the intensity of a fluorescent light in the ThreeBond 3065 of ThreeBond Co., Ltd. shown in FIG. 8.

FIG. 11 illustrates a profile showing the relation between the irradiation power of the ultraviolet ray for curing 54 and the intensity of the fluorescent light emitted from the ultraviolet curing resin material of ThreeBond 3065 shown in FIG. 8. As shown in FIG. 11, the intensity of the fluorescent light is measured with the irradiation power which is 50% and 10% assuming that the irradiation power of the ultraviolet ray for curing 54 shown in FIG. 8 is 100%.

As apparent from FIG. 11, when the irradiation power is 50% and 100%, the intensity of the fluorescent light rapidly increases just after the start of the irradiation and then continuously increases although its increasing speed falls down about 60 seconds after the start of the irradiation. When the irradiation power is 10%, the absolute value of the intensity of the fluorescent light becomes smaller than at 50% or 100%. When the irradiation power is 100%, the absolute value of the intensity of the fluorescent light becomes smaller than at 50%.

The intensity of the fluorescent light after a considerable length of time has passed is substantially constant regardless of the irradiation power.

Figure 12:
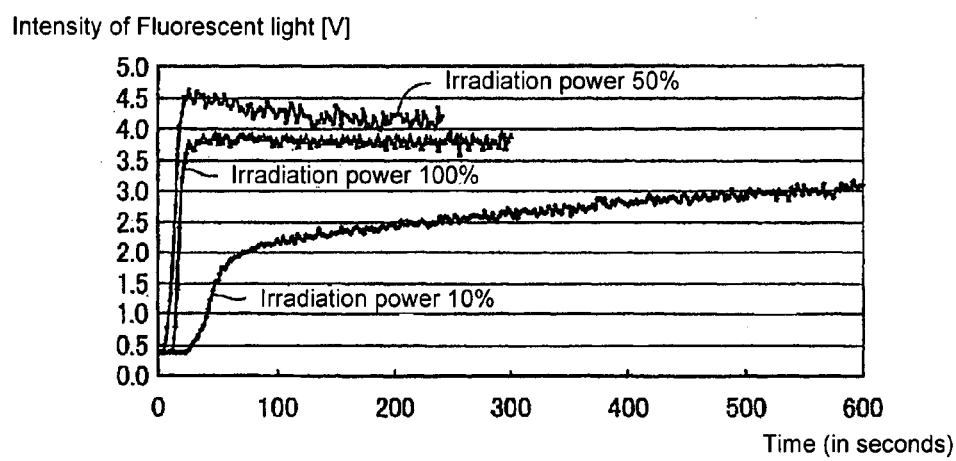
FIG. 12 shows a diagram of the relation between the irradiation power of an ultraviolet ray for curing and the intensity of a fluorescent light in the ThreeBond 3114B of ThreeBond Co., Ltd. shown in FIG. 9.

FIG. 12 illustrates a profile showing the relation between the irradiation power of the ultraviolet ray for curing 54 and the intensity of the fluorescent light emitted from the ultraviolet curing resin material of ThreeBond 3114B shown in FIG. 9. As shown in FIG. 12, the intensity of the fluorescent light is measured with the irradiation power which is 50% and 10% assuming that the irradiation power of the ultraviolet ray for curing 54 shown in FIG. 9 is 100%.

As apparent from FIG. 12, when the irradiation power is 50%, the intensity of the fluorescent light rapidly increases just after the start of the irradiation and then gradually decreases while its increasing speed falls down about 40 seconds after the start of the irradiation. When the irradiation power is 10%, the absolute value of the intensity of the fluorescent light becomes smaller than at 50% or 100%. When the irradiation power is 100%, the absolute value of the intensity of the fluorescent light becomes smaller than at 50%.

(Features of a Change with Time in the Intensity of Fluorescent Light)

The change with time in the intensity of fluorescent light has several features as explained below. The features are separately explained in conjunction with the views of the inventors.

As the first feature, the curing level increases just after the start of the irradiation of the ultraviolet ray for curing 54 while the intensity of the fluorescent light remains unchanged at a low level for a while after the start of the irradiation of the ultraviolet ray for curing 54 or temporarily declines in some types of the ultraviolet curing resin material. It is assumed that the light energy received is consumed in chemical actions such as for generating active species during a certain period of time after the start of the irradiation of the ultraviolet ray for curing 54, but not for promoting the emission of the fluorescent light. The reason why the intensity of the fluorescent light declines may be that the chemical actions generate heat of which the energy increases the temperature of the ultraviolet curing resin material and retards the emission of the fluorescent light.

As the second feature, the intensity of the fluorescent light increases at a greater speed after a certain period of time from the start of the irradiation of the ultraviolet ray for curing 54. It is assumed that after the generation of active species, the action of the photo polymerization initiator for converting the absorbed light energy of the ultraviolet ray into the emission of the fluorescent light starts and increases its share with time.

As the third feature, the intensity of the fluorescent light gradually increases or its increase stops in some types of the ultraviolet curing resin material. It is assumed at this stage that the photo polymerization initiator is entirely consumed and permits no more generation of active species. Some types of the ultraviolet curing resin material reach the final level of the curing level by this stage while other types require more time before the curing level reaches its final level. Even if the ultraviolet curing resin material requires more time, its curing action (the polymerizing action) does not stop regardless of no generation of the active species but proceeds until the curing level reaches its final level.

As the fourth feature, some types of the ultraviolet curing resin material continuously increase, although slow in speed, in the intensity of its emitting fluorescent light after the increasing speed becomes moderate. Other types decline in the intensity of its emitting fluorescent light although at a small rate. When the intensity of the fluorescent light temporarily decreases regardless of the irradiation (the power and the duration) of the ultraviolet ray for curing 54, it increases soon. In any case, many types of the ultraviolet curing resin material emit the fluorescent light at a greater level than that where the intensity of the fluorescent light gradually increases or declines temporarily before increased again, for as a long period as a few days.

It is hence concluded that when the photo polymerization initiator has finished the generation of the active species, the energy of the ultraviolet ray received is not all consumed for the emission of the fluorescent light but used for other actions. As the polymer just after the end of the polymerizing action (the curing action) accumulates a structural stress at the molecular level, there is an easing stage for releasing gradually the stress. A portion of the energy of the ultraviolet ray may hence be consumed for suppressing the release of the stress.

As the fifth feature, the intensity of the fluorescent light (for example, at the level where the increase stops) depends on the irradiation power of the ultraviolet ray for curing 54. When the irradiation power of the ultraviolet ray for curing 54 remains small, the intensity of the fluorescent light increases in proportion to the irradiation power. The irradiation power has a threshold below which the intensity of the fluorescent light is largely increased. When the irradiation power exceeds the threshold, the intensity of the fluorescent light may decline.

It is hence assumed that when the irradiation power is received at a higher level than the threshold, the ultraviolet curing resin material develops a heavy structural stress therein which then disturbs the emission of the fluorescent light and declines its intensity. When the irradiation power is received at a lower level than the threshold, the ultraviolet curing resin material commences its curing action particularly at the region near the outer surface at the initial stage. This curing action at the initial stage may prevent the ultraviolet ray for curing 54 from penetrating deeply into the ultraviolet curing resin material, hence declining the intensity of the fluorescent light.

In consideration of the above described features, the state estimator 102 conducts estimation of a state of the ultraviolet curing resin material through following the procedure below.

(Estimation of the State of Ultraviolet Curing Resin Material)

Figure 13:
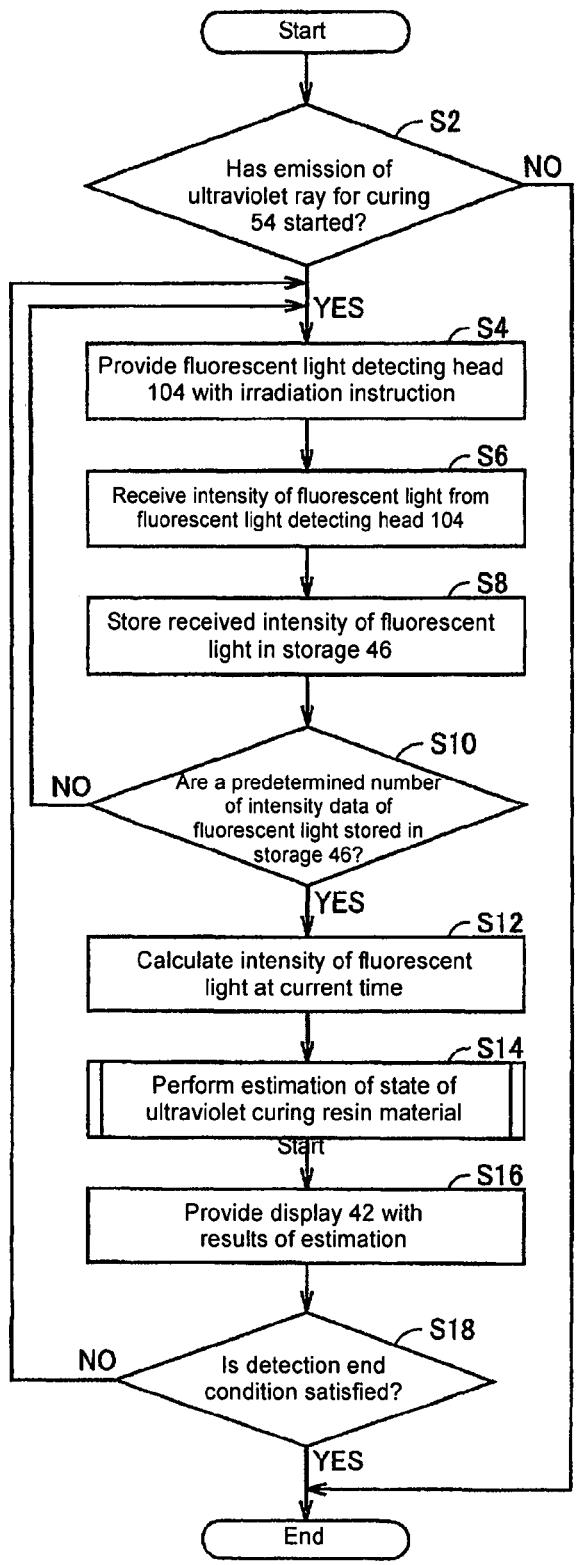
FIG. 13 shows a flowchart of a procedure of a method for estimating a state according to the present invention.

FIG. 13 is a flowchart showing the procedure of estimating a state according to the embodiment of the present invention.

As shown in FIG. 13, the CPU 40 determines whether or not the emission of the ultraviolet ray for curing 54 is started in response to the irradiation state signal from the curing ultraviolet ray emitting apparatus 200 (Step S2). When the emission of the ultraviolet ray for curing 54 is not started (NO at Step S2), the CPU 40 returns to "start".

When the emission of the ultraviolet ray for curing 54 is started (YES at Step S2), the CPU 40 provides the fluorescent light detecting head 104 with an irradiation instruction (Step S4). The fluorescent light detecting head 104 then emits the ultraviolet ray for detection 50 towards the ultraviolet curing resin material to be examined. The CPU 40 receives from the fluorescent light detecting head 104 a measurement of the intensity of the fluorescent light emitted from the photo polymerization initiator included in the ultraviolet curing resin material upon receiving the ultraviolet ray for detection 50 (Step S6).

The CPU 40 then stores the measurement of the intensity of the fluorescent light in the storage 46 (Step S8) and examines whether or not the measurements of the intensity of the fluorescent light are accumulated to a predetermined number in the storage 46 (Step S10). When the measurements of the intensity of the fluorescent light are accumulated not to the predetermined number (NO at Step S10), the CPU 40 returns to Step S4.

When the measurements of the intensity of the fluorescent light are accumulated to the predetermined number (YES at Step S10), the CPU 40 reads out the predetermined number of the measurements of the intensity of the fluorescent light from the storage 46 and carries out a (moving) average calculating process to determine the intensity of the fluorescent light at the moment (Step S12).

Using the intensity of the fluorescent light determined, the CPU 40 conducts estimation processing of a state of the ultraviolet curing resin material (Step S14). More specifically, the CPU 40 retrieves and conducts a sub routine which includes steps as will be described later.

Then, the CPU 40 outputs a result of the state estimation to the display 42 (Step S16) and determines whether or not the condition for terminating the detection is satisfied (Step S18). The condition for terminating the detection includes that a particular length of time has elapsed after the start of irradiation of the ultraviolet ray for curing 54 or that the curing level is determined to have reached its maximum level in Step S14. When the condition for terminating the detection is not satisfied (NO at Step S18), the CPU 40 returns to Step S4. When the condition for terminating the detection is satisfied (YES at Step S18), the CPU 40 returns to "start".

(Estimation of the State of Photo Polymerization Initiator from the Speed of Change in Intensity of Fluorescent Light)

As described above, the intensity of the fluorescent light changes depending on the chemical state of the photo polymerization initiator. The moment of time when the photo polymerization initiator has substantially been consumed is then estimated based on the speed of change in the intensity of the fluorescent light from the detected change with time in the intensity of the fluorescent light. In many cases, the ultraviolet curing resin material includes a generous amount of the photo polymerization initiator which equals the theoretically required amount multiplied by a marginal rate determined from the conditional factors including the yield and the temperature, fluctuations. The statement "the photo polymerization initiator has substantially been consumed" means that a sufficient quantity of active species (radicals and acids) for promoting the (curing) reactive action are generated by the photo polymerization initiator. This will remain unchanged throughout the description.

It is assumed that the increase of the intensity of the fluorescent light is suppressed when the photo polymerization initiator has substantially been consumed. Accordingly, it can be decided that the photo polymerization initiator has substantially been consumed when the intensity of the fluorescent light after being increased is declined in an increasing speed, halted in the increase (i.e. the speed of the increase is zero), or decreased (i.e. the speed of the increase is a negative rate).

Figure 14:
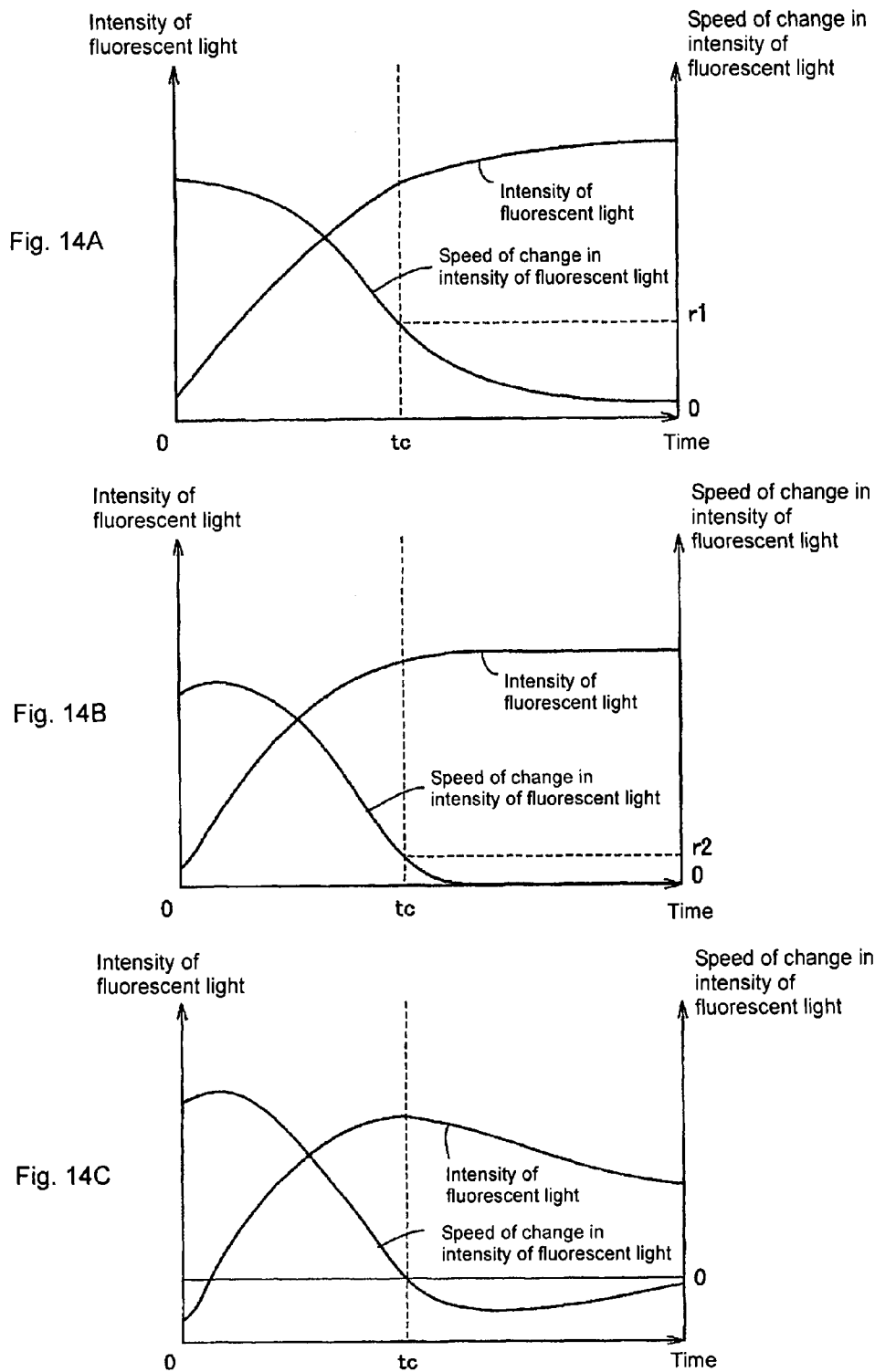
FIGS. 14A-14C show diagrams illustrating estimation of a state of a photo polymerization initiator based on a speed of change in an intensity of a fluorescent light.

FIG. 14 illustrates profiles showing the estimation of a state of the photo polymerization initiator based on the speed of change in the intensity of the fluorescent light. In FIG. 14, the time for starting the irradiation of the ultraviolet ray for curing 54 (FIG. 1) is set as a reference time (at zero).

FIG. 14A illustrates that after being increased in the intensity of the fluorescent light, the speed of the increase is declined as from a particular point of time.

FIG. 14B illustrates that after being increased in intensity of the fluorescent light, the increase stops as from a particular point of time.

FIG. 14C illustrates that after being increased in intensity of the fluorescent light, it is declined as from a particular point of time.

Referring to 14A, it is assumed that the photo polymerization initiator has substantially been consumed at the time tc when the speed of change (a rate of change for a unit time) in the intensity of the fluorescent light is decreased to below r1. More particularly, the time when the photo polymerization initiator has substantially been consumed is estimated by, after the start of the irradiation of the ultraviolet ray 54, detecting the time when the speed of the increase in the intensity of the fluorescent light is declined after being increased in the intensity.

Referring to FIG. 14B, it is assumed that the photo polymerization initiator has substantially been consumed at the time tc when the speed of change in the intensity of the fluorescent light is decreased to below r2 or close to zero. More particularly, the time when the photo polymerization initiator has substantially been consumed is estimated by, after the start of the irradiation of the ultraviolet ray for curing 54, detecting the time when the increase of the intensity of the fluorescent light stops after being increased in the intensity Referring to FIG. 14C, it is assumed that the photo polymerization initiator has substantially been consumed at the time tc when the speed of change in the intensity of the fluorescent light turns into a negative rate. More particularly, the time when the photo polymerization initiator has substantially been consumed is estimated by, after the start of the irradiation of the ultraviolet ray for curing 54, detecting the time when the intensity of the fluorescent light is declined after being increased.

Figure 15:
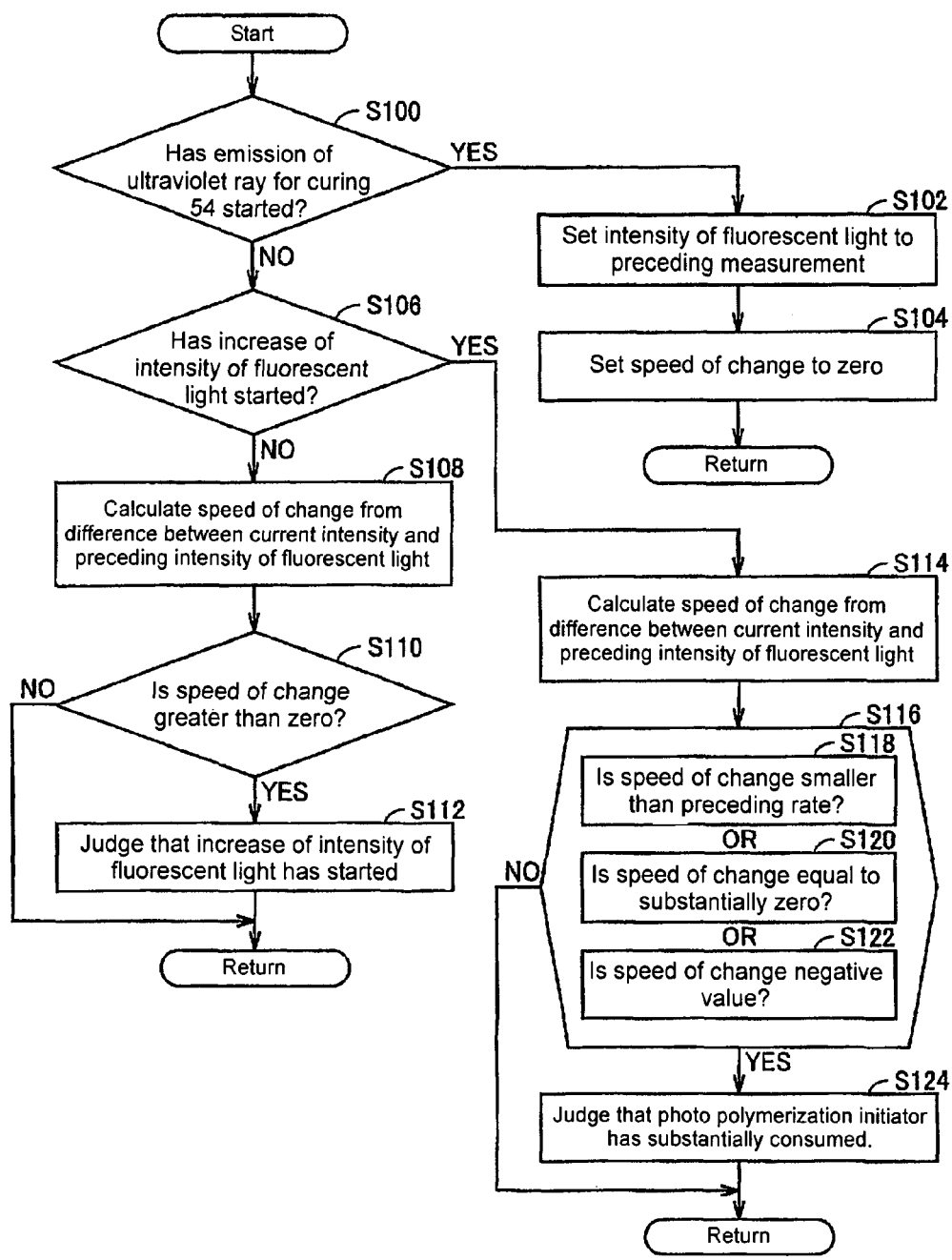
FIG. 15 shows a flowchart of estimation of a state of a photo polymerization initiator based on a speed of change in an intensity of a fluorescent light.

FIG. 15 is a flowchart showing the procedure of estimating a state of the photo polymerization initiator based on the speed of change in the intensity of the fluorescent light. The flowchart shown in FIG. 15 can be defined as a sub-routine called up during the state estimating processing shown in FIG. 13 (Step 14).

As shown in FIG. 15, the CPU 40 determines whether or not the irradiation of the ultraviolet ray for curing 54 has just started (Step S100). When the irradiation of the ultraviolet ray for curing 54 has just started (YES at Step S100), the CPU 40 sets the intensity of the fluorescent light with the previously given level (Step S102) and the speed of change to zero (Step S104). The CPU 40 then returns to the preceding processing.

When the irradiation of the ultraviolet ray for curing 54 has not started (NO at Step S100), the CPU 40 determines whether or not the increase of the intensity of the fluorescent light has just started (Step S106). The statement that the increase of the intensity of the fluorescent light has just started means just after the CPU 40 judges the start of the increase of the intensity of the fluorescent light at Step S112 as will be explained later.

When the increase of the intensity of the fluorescent light has not started (NO at Step S106), the CPU 40 calculates the speed of change from a difference between the current measurement and the preceding measurement of the intensity of the fluorescent light (Step S108). The CPU 40 then determines whether or not the calculated speed of change is greater than zero (Step S110). When the calculated speed of change is greater than zero (YES at Step S110), the CPU 40 judges the start of the increase of the intensity of the fluorescent light (Step S112) and then returns to the preceding processing. When the calculated speed of change is not greater than zero (NO at Step S110), the CPU 40 returns to the preceding processing. The reference value for judging the start of the increase of the intensity of the fluorescent light may be a predetermined positive value except zero.

When the intensity of the fluorescent light is determined that its increase has started (YES at Step S106), the CPU 40 calculates the speed of change from a difference between the current measurement and the preceding measurement of the intensity of the fluorescent light (Step S114). The CPU 40 then determines whether or not the calculated speed of change has a specific point (Step S116). More specifically, the CPU 40 determines one of whether or not the calculated speed of change is smaller than the preceding speed of change (Step S118), whether or not the calculated speed of change is substantially zero (Step S120) and whether or not the calculated speed of change is a negative rate (Step S122). The criteria for the determination may be predetermined by the user. When the speed of change in the intensity of the fluorescent light has a specific point (YES at Step S116), the CPU 40 determines that the photo polymerization initiator has substantially been consumed (Step S124) and then returns to the preceding processing.

When the speed of change in the intensity of the fluorescent light has no specific point (NO at Step S116), the CPU 40 returns to the preceding processing.

The estimation of a state of the photo polymerization initiator based on the speed of change in the intensity of the fluorescent light permits all the points of time when the photo polymerization initiator for promoting the curing action (the polymerizing action) of the ultraviolet curing resin material reacts to be easily estimated. After the irradiation of the ultraviolet ray for curing 54 is terminated, the curing action of the ultraviolet curing resin material continues to proceed. Accordingly, the irradiation of the ultraviolet ray for curing 54 needs not to be continued until the curing action of the ultraviolet curing resin material is completed but can be canceled at the time when the photo polymerization initiator has substantially been consumed. This allows the duration of time for irradiation of the ultraviolet ray for curing 54 to the ultraviolet curing resin material to be optimized, hence improving the production efficiency of, e.g., production lines.

(Estimation of the Curing Level Based on the Speed of Change in the Intensity of Fluorescent Light)

As described, the intensity of the fluorescent light changes corresponding to the degree of reaction in the polymerizing (curing) action of the ultraviolet curing resin material. The time when the ultraviolet curing resin material reaches its maximum curing level is estimated based on the speed of change in the intensity of the fluorescent light which is one of the detected changes with time in the intensity of the fluorescent light. While the ultraviolet curing resin material is commonly specified with its standard value of the curing level (shown in its catalogue) by e.g. the manufacturers, the "maximum curing level" equals to a curing level which the ultraviolet curing resin material can reach and will be referred throughout the description. The curing level is not always equal to the standard value (shown in the catalogue).

When the ultraviolet curing resin material has reached its maximum curing level, it starts interrupting the increase in the intensity of the fluorescent light to be emitted and measured. It is hence assumed that the ultraviolet curing resin material has reached its maximum curing level when the intensity of the fluorescent light after being increased is declined in an increasing speed, halted in the increase (i.e., the speed of change is zero), or decreased (i.e., the speed of change turns into a negative rate).

The method and the flowchart for finding the specific point in the speed of change in the intensity of the fluorescent light are the same as those shown in FIGS. 14 and 15 and will be explained in no more detail.

According to the state estimation of the curing level based on the speed of change in the intensity of the fluorescent light described above, the time when the ultraviolet curing resin material reaches its maximum curing level can easily be estimated. This will prevent any deficiency of the curing action (the polymerizing action) of the ultraviolet curing resin material caused by shortage of the irradiation time of the ultraviolet ray for curing 54. In particular, although the ultraviolet curing resin material tends to significantly change in property by temperature or by aging, its curing action can favorably be controlled by this procedure optimizing the period of irradiation of the ultraviolet ray at each point of time during the process.

(Estimation of the Curing Level Based on an Amount of Change in the Intensity of Fluorescent Light)

As described, the intensity of the fluorescent light changes corresponding to a degree of the polymerizing (curing) action in the ultraviolet curing resin material. The time when the ultraviolet curing resin material reaches a particular curing level is estimated based on an amount of change in the intensity of the fluorescent light which is one of the detected changes with time in the intensity of the fluorescent light. For example, it is estimated that the ultraviolet curing resin material has reached a particular curing level when a difference or a ratio between intensities of the fluorescent light before and after the start of the increase exceeds a predetermined threshold. More particularly, it can be decided that the ultraviolet curing resin material has reached a particular curing level by properly selecting the amount of change in the intensity of the fluorescent light as a reference of judgment. It is decided at the point of time that the polymerizing action of the ultraviolet curing resin material has been fulfilled. Using a small value of the amount of change in the intensity of the fluorescent light as a reference of judgment, it can be decided that the curing action of the ultraviolet curing resin has reached to a particular level lower than the maximum level. In the latter case, it is determined from the amount of change in the intensity of the fluorescent light that the curing action has progressed to a particular curing level at the time, for example, where an object temporarily secured by the ultraviolet curing resin material is not largely displaced. Most types of the ultraviolet curing resin material have a property that the curing action is gradually progressed by a chain reaction without the irradiation of the ultraviolet ray when its polymerization has been progressed to a particular level by the irradiation of the ultraviolet ray. When the ultraviolet curing resin material at a half the level of curing is heated, its chain reaction is accelerated. Such a technique as canceling the irradiation of the ultraviolet ray for curing at the stage where the ultraviolet curing resin material is not completely cured is used for temporarily bonding an object with the ultraviolet curing resin material. After bonded temporarily with a not cured, soft form of the ultraviolet curing resin material, the object can finely be adjusted in positioning. The technique may also be employed for heating and curing a number of products in a semi-cured form at the bonding locations through irradiation of ultraviolet ray within a short time. Accordingly, the duration of time required for curing can be shortened as compare with the irradiation of ultraviolet ray until each curing location reaches its maximum curing level.

Figure 16:
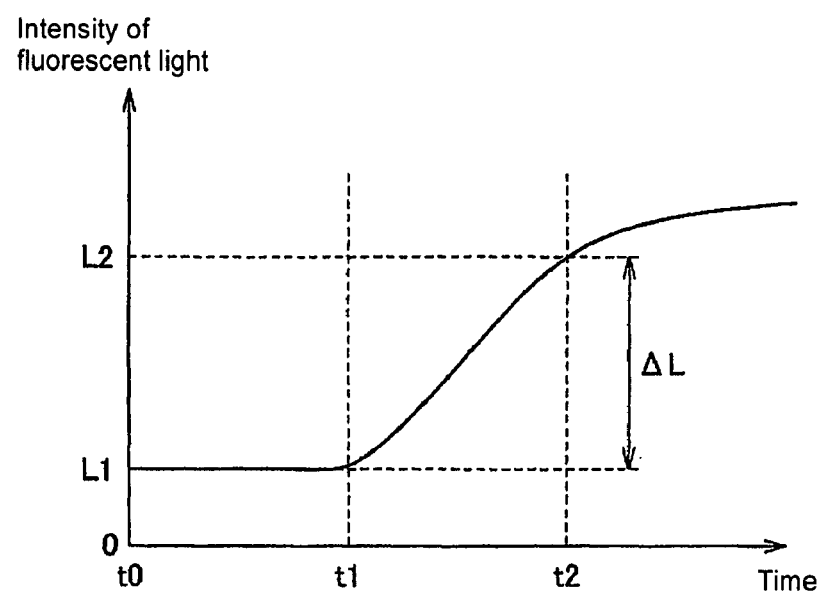
FIG. 16 shows a diagram illustrating estimation of the curing level based on an amount of change in an intensity of a fluorescent light.

FIG. 16 is a profile showing the estimation of the curing level based on the amount of change in the intensity of the fluorescent light. In FIG. 16, the start of irradiation of the ultraviolet ray for curing 54 (FIG. 1) is designated as a reference point of time (at zero).

Assuming in FIG. 16 that the start of the increase of the intensity of the fluorescent light is t1 after the irradiation of the curing ultraviolet ray 54 is commenced at t0, it is determined that the ultraviolet curing resin material reaches its maximum curing level at the time t2 when a difference $\Delta L(=L2-L1)$ between the measurement L1 of the intensity of the fluorescent light immediately after t0 or before t1 and the measurement L2 of the intensity of the fluorescent light just after the start of the increase of the intensity of the fluorescent light exceeds a predetermined threshold.

Alternatively, it is determined that the ultraviolet curing resin material reaches its maximum curing level at the time t2 when a ratio (=L2/L1) of one measurement L2 to the other measurement L1 of the intensity of the fluorescent light exceeds a predetermined threshold.

Figure 17:
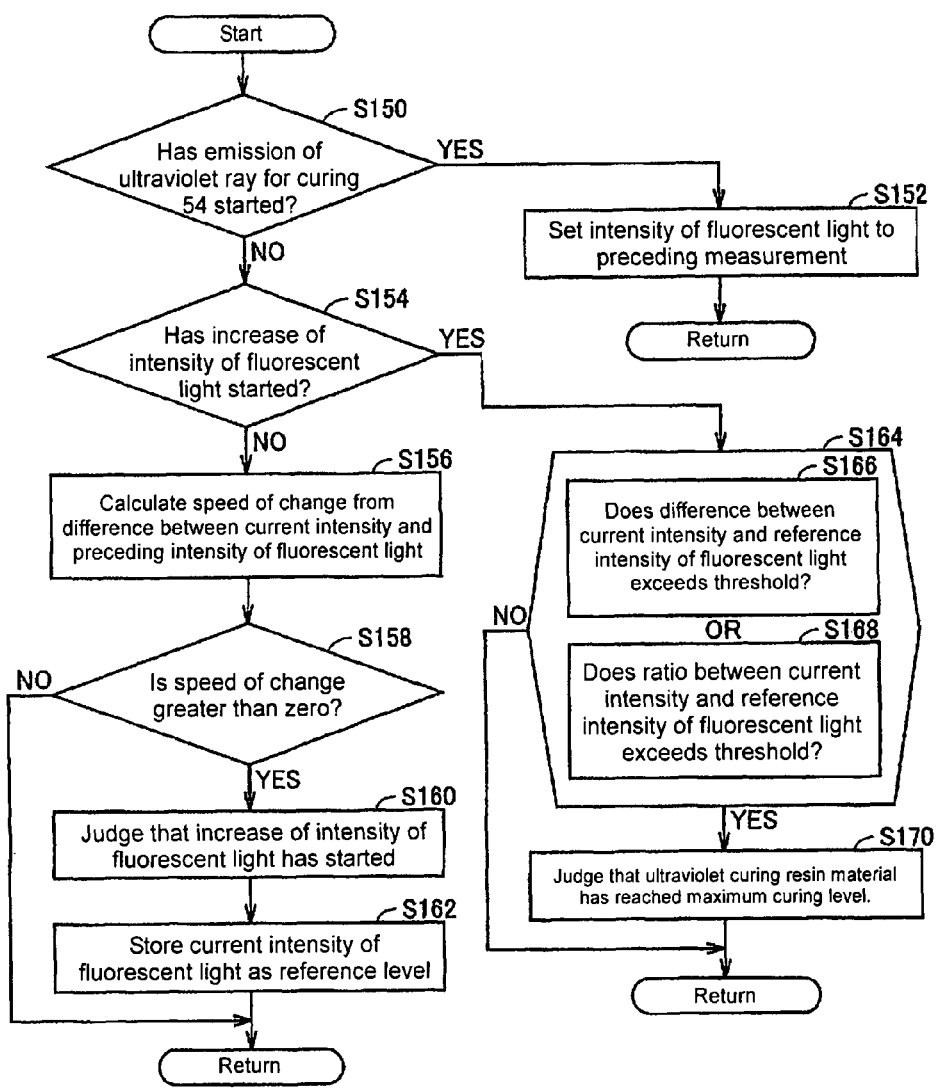
FIG. 17 shows a flowchart of estimation of the curing level based on an amount of change in an intensity of a fluorescent light.

FIG. 17 is a flowchart showing a procedure of the estimate of the curing level from the amount of a change in the intensity of the fluorescent light. The flowchart shown in FIG. 17 may be defined as a sub routine which is called at the step of estimating the state (Step S14) shown in FIG. 13.

As shown in FIG. 17, the procedure starts with the CPU 40 examining whether or not the irradiation of the ultraviolet ray for curing 54 has just started (Step S150). When the irradiation of the ultraviolet ray for curing 54 has just started (YES at Step S150), the CPU 40 examines whether or not the increase of the intensity of the fluorescent light has started (Step S154). The statement that the increase of the intensity of the fluorescent light has started equals the judgment of the CPU 40 at Step S160 which will be explained later.

When the ultraviolet ray for curing 54 has not started (NO at Step S150), the CPU 40 determines whether or not the intensity in the fluorescent light has just started to increase (Step S154). The expression that the intensity in the fluorescent light has just started to increase means a state after the CPU 40 determines the start of increase in the fluorescent speed in Step S160 as described later.

When the increase of the intensity of the fluorescent light has not started (NO at Step S154), the CPU 40 calculates the speed of change from a difference between the current measurement and the preceding measurement of the intensity of the fluorescent light (Step S156). The CPU 40 then examines whether or not the calculated speed of change is greater than zero (Step S158). When the calculated speed of change is greater than zero (YES at Step S158), the CPU 40 judges the start of the increase of the intensity of the fluorescent light (Step S160), saves the measurement of the intensity of the fluorescent light at the time as a reference intensity of the fluorescent light (Step S162), and then returns to its preceding routine. When the calculated speed of change is not greater than zero (NO at Step S158), the CPU 40 returns to its preceding routine. The reference value for examining the start of the increase of the intensity of the fluorescent light is not limited to zero but may be any favorable positive value.

When the intensity of the fluorescent light is determined that its increase has started (YES at Step S154), the CPU 40 examines whether or not the amount of a change from the reference level in the intensity of the fluorescent light exceeds a predetermined threshold (Step S164). More particularly, the CPU 40 examines either whether or not a difference between the current measurement and the threshold level of the intensity of the fluorescent light exceeds a threshold (Step S166) or whether or not a ratio of the current measurement to the threshold level of the intensity of the fluorescent light exceeds a threshold (Step S168). The manner of the examination may be predetermined as a reference manner by the user. When the amount of a change from the reference level in the intensity of the fluorescent light exceeds the predetermined threshold (YES at Step S164), the CPU 40 determines that the ultraviolet curing resin material has reached its maximum curing level (Step S170) and then returns to its preceding routine.

When the amount of a change from the reference level in the intensity of the fluorescent light does not exceed the predetermined threshold (NO at Step S164), the CPU 40 returns to its preceding routine.

The estimation of the curing level from the amount of a change in the intensity of the fluorescent light permits the point of time when the ultraviolet curing resin material reaches its maximum curing level to be easily estimated. This will prevent any deficiency of the curing action (the polymerizing action) of the ultraviolet curing resin material caused by shortage of the irradiation of the ultraviolet ray for curing 54. In particular, the ultraviolet curing resin material tends to be fairly changed in the property by temperature or by aging and its curing action can favorably be controlled by this procedure optimizing the period of irradiation of the ultraviolet ray at each primary point of time during the process.

(Estimation of the Curing Level from the Absolute Value of Intensity of Fluorescent Light)

As described, the intensity of the fluorescent light changes corresponding to the degree of reaction in the polymerizing (curing) action of the ultraviolet curing resin material. The time when the ultraviolet curing resin material has been elevated to a desired curing level is estimated from the absolute value of the intensity of the fluorescent light which is one of measurements of the change with time in the intensity of the fluorescent light. For example, it is determined from the time when the intensity of the fluorescent light exceeds a predetermined threshold that the ultraviolet curing resin material has been elevated to a desired curing level. The desired curing level equals the maximum curing level or any other smaller degree than the maximum degree as described.

Figure 18:
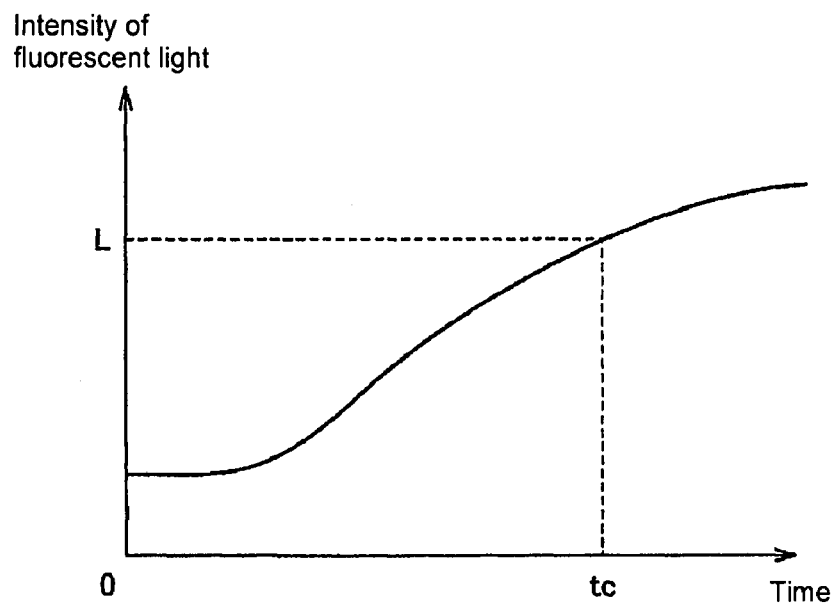
FIG. 18 shows a diagram illustrating estimation of the curing level based on absolute value of an intensity of a fluorescent light.

FIG. 18 is a profile showing the estimation of the curing level from the absolute value of the intensity of the fluorescent light. In FIG. 18, the start of irradiation of the ultraviolet ray for curing 54 (FIG. 1) is designated as a reference point of time (at zero).

As shown in FIG. 18, the ultraviolet curing resin material reaches its maximum curing level at the time tc when the intensity of the fluorescent light is increased to a threshold L after the start of the irradiation of the ultraviolet ray for curing 54.

Figure 19:
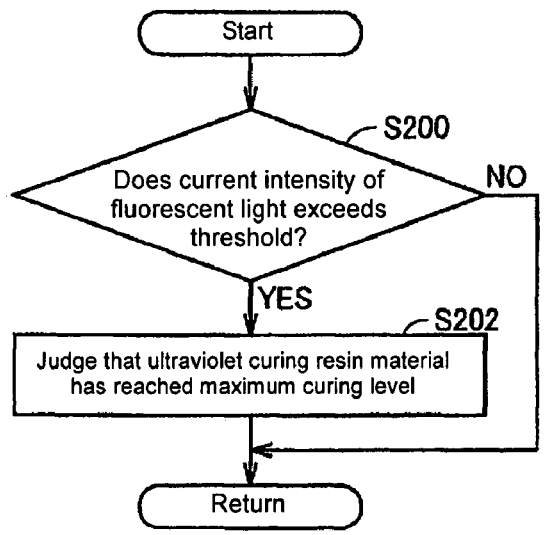
FIG. 19 shows a flowchart of estimation of the curing level based on absolute value of an intensity of a fluorescent light.

FIG. 19 is a flowchart showing a procedure of the estimate of the curing level from the absolute value of the intensity of the fluorescent light. The flowchart shown in FIG. 19 may be defined as a sub routine which is called at the step of estimating the state (Step S14) shown in FIG. 13.

As shown in FIG. 19, the procedure starts with the CPU 40 examining whether or not the current measurement of the intensity of the fluorescent light exceeds the threshold (Step S200). When the current measurement of the intensity of the fluorescent light exceeds the threshold (YES at Step S200), the CPU 40 determines that the ultraviolet curing resin material has reached its maximum curing level (Step S202) and then returns to its preceding routine.

When the current measurement of the intensity of the fluorescent light does not exceed the threshold (NO at Step S200), the CPU 40 returns to its preceding routine.

It is assumed that the threshold to be predetermined is varied depending on the type and quantity of the ultraviolet curing resin material and the irradiation conditions of the curing ultraviolet ray 54. Therefore, sets of the thresholds have to be calculated from a series of experiments in relation to the type and quantity of the ultraviolet curing resin material and the irradiation conditions of the curing ultraviolet ray 54.

The estimation of the curing level from the absolute value the intensity of the fluorescent light permits the point of time when the ultraviolet curing resin material reaches its maximum curing level to be easily estimated. This will prevent any deficiency of the curing action (the polymerizing action) of the ultraviolet curing resin material caused by shortage of the irradiation of the ultraviolet ray for curing 54. Particularly in case that the curing action is repeatedly conducted under the relatively stable conditions, it can favorably be controlled by this procedure optimizing the irradiation period at each primary point of time during the process.

(Estimation of the State of Ultraviolet Curing Resin Material from the Comparison Between Change with Time and its Reference Level)

In the production line, the ultraviolet curing resin material of a particular type is repeatedly subjected to the curing action under substantially a uniform irradiation condition. It is hence practical and effective for estimating the state of the ultraviolet curing resin material to preliminarily obtain a typical change with time in the intensity of the fluorescent light from each type of the ultraviolet curing resin material and compare the typical change with a measurement of the change with time.

FIG. 20 illustrates profiles showing the estimation of the state of the ultraviolet curing resin material from the comparison between a change with time and its reference profile. In FIG. 20, the start of irradiation of the ultraviolet ray for curing 54 (FIG. 1) is designated as a reference point of time (at zero).

Figure 20A:
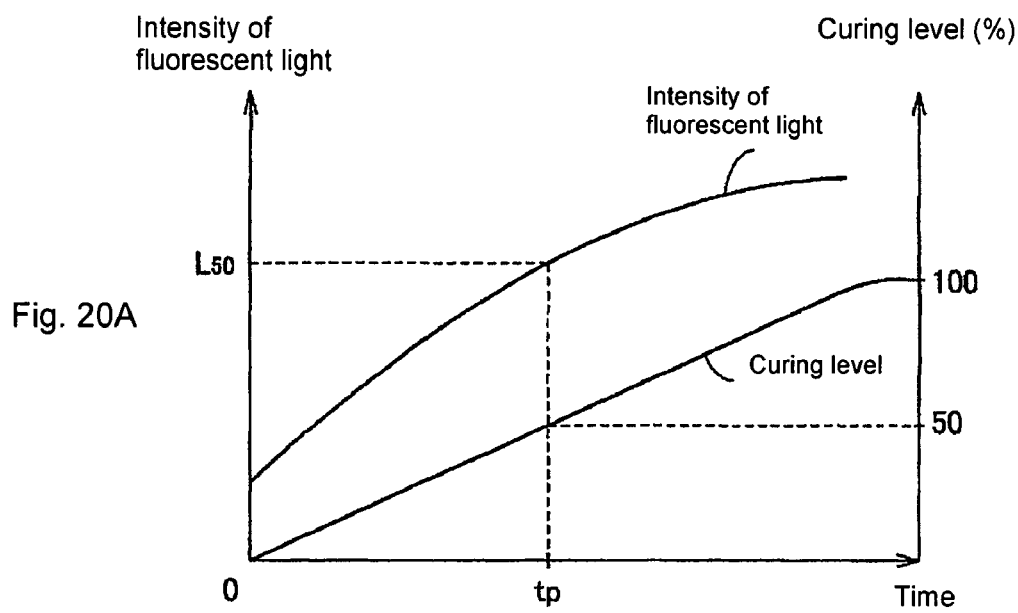
FIGS. 20A and 20B show diagrams illustrating estimation of a state of an ultraviolet curing resin material based on comparison between a change with time and a reference value.

FIG. 20A shows an example of the reference profile of the change with time which is predetermined.

Figure 20B:
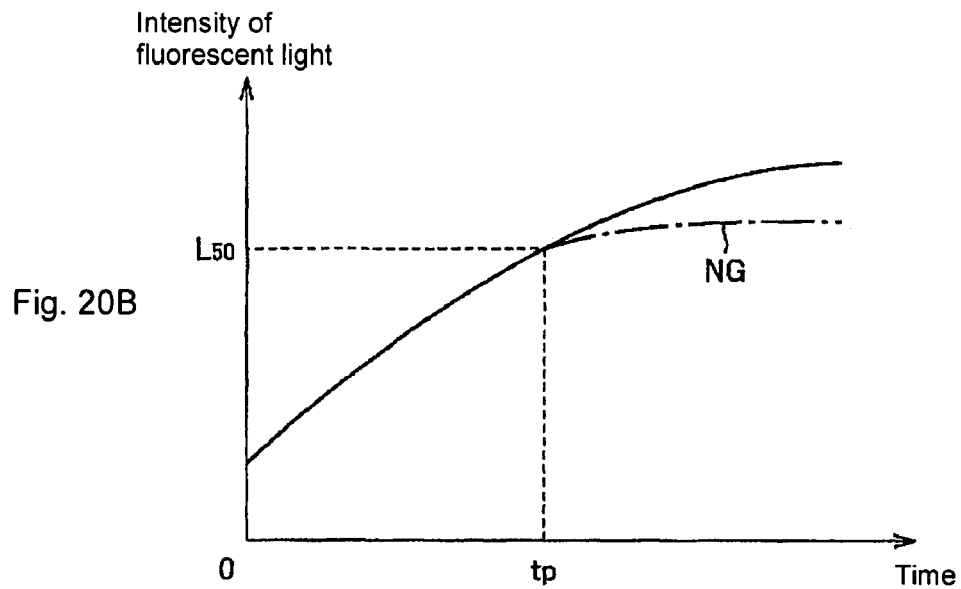

FIG. 20B shows a change with time in the intensity of the fluorescent light from the ultraviolet curing resin material under the same irradiation condition as of FIG. 20A.

Referring to FIG. 20A, the relationship between the curing level (100% at the maximum) and the intensity of the fluorescent light at each type of the ultraviolet curing resin material to be examined has been recorded in advance through a series of experiments by the user for determining the reference of a change with time. The change with time may be received from a manufacturer of the ultraviolet curing resin material or the state estimating apparatus or prepared by the user repeatedly measuring multiple relevant samples of the ultraviolet curing resin material.

The change with time in the intensity of the fluorescent light shown in FIG. 20A is denoted where the intensity is L50 at 50% of the curing level and the curing level turns to 50% at the time tp.

It is determined from FIG. 20B that the curing level in the ultraviolet curing resin material to be examined turns to 50% at the time tp where the intensity of the fluorescent light after the start of the irradiation of the ultraviolet ray for curing is increased to L50. More specifically, the measurement of the intensity of the fluorescent light is examined how its change with time geometrically matches the reference profile shown in FIG. 20A and then, the state of the ultraviolet curing resin material (at the target curing level) can be estimated from the result of the geometrical examination.

When the change with time in the intensity of the fluorescent light after the time tp is largely discrepant from the reference profile shown in FIG. 20A (as denoted by NG), it is then determined that the ultraviolet curing resin material to be examined has a fault. The fault may include selection error of the type of the ultraviolet curing resin material, error of the weight of the ultraviolet curing resin material, deterioration in quality of the ultraviolet curing resin material, undesired progress of the curing action of the ultraviolet curing resin material during the storage, and variations of the irradiation condition (displacement of the ultraviolet ray irradiating head, discrepancy of the irradiation power, and mechanical failure).

Figure 21:
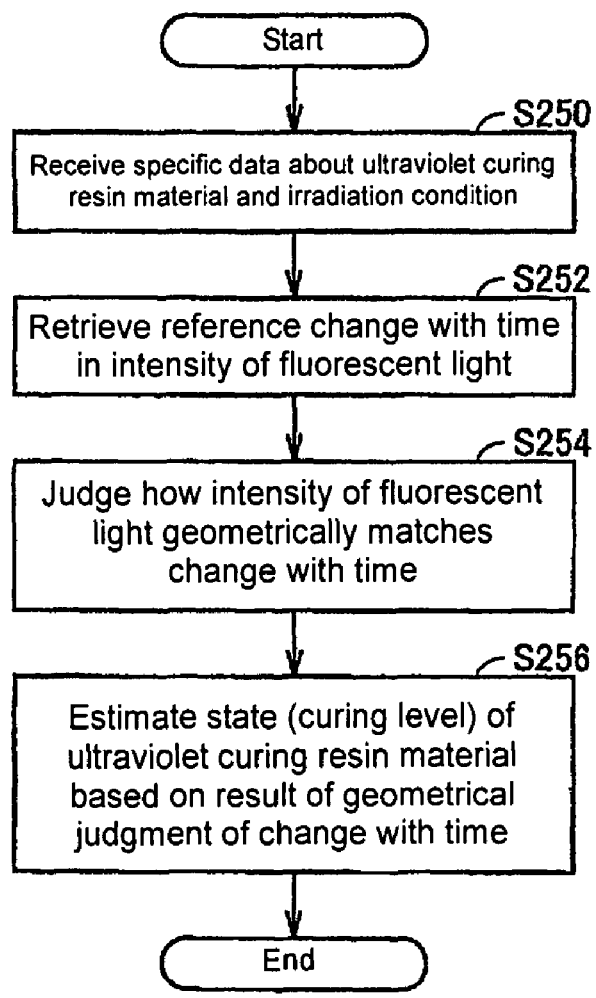
FIG. 21 shows a flowchart of estimation of a state of an ultraviolet curing resin material based on comparison between a change with time and a reference value.

FIG. 21 is a flowchart showing the procedure of estimating the state of the ultraviolet curing resin material from the comparison between a change with time and its reference profile. The flowchart shown in FIG. 21 may be designated as a sub routine which is called at the estimating action (Step S14) shown in FIG. 13.

As shown in FIG. 21, the procedure starts with the CPU 40 receiving a specific data about the ultraviolet curing resin material and the irradiation condition from the user (Step S250) and retrieving the reference profile of a change with time in the intensity of the fluorescent light from the storage 46 in response to the specific data (Step S252). The CPU 40 then examines how the current measurement of the intensity of the fluorescent light geometrically matches the reference profile of the change with time (Step S254).

The CPU 40 estimates the state (the curing level) of the ultraviolet curing resin material from the result of examination or comparison with the reference profile of the change with time (Step S256). The CPU 40 returns to its preceding routine.

For the comparison with the reference profile of the change with time, not only the current measurement of the intensity of the fluorescent light but also a characteristic change from one moment to another in the intensity of the fluorescent light may be used.

As described, the procedure of estimating the state of the ultraviolet curing resin material from the comparison with the reference profile of a change with time allows the relative state of the ultraviolet curing resin material to the reference state of the change with time in the intensity of the fluorescent light to be easily calculated. Also, through monitoring the discrepancy from the reference profile of the change with time, any fault in the ultraviolet curing resin material cab readily be found.

(Estimation of the State of Ultraviolet Curing Resin Material from Length of Time Required for the Intensity of Fluorescent Light Causing a Specific Change with Time)

As described with the previous procedure of estimating the state of the ultraviolet curing resin material, it is practical and effective for estimating the state of the ultraviolet curing resin material to preliminarily obtain a typical change with time in the intensity of the fluorescent light from each type of the ultraviolet curing resin material and compare the typical change with a measurement of the change with time, particularly in case that one type of the ultraviolet curing resin material is repeated processed. For example, a length of time required for the intensity of the fluorescent light causing a specific change with time is measured and its measurement is compared with a reference length of time which is predetermined thus to estimate the state of the ultraviolet curing resin material.

FIG. 22 illustrates profiles showing the estimation of the state of the ultraviolet curing resin material from the comparison of a length of time required for the intensity of the fluorescent light causing a specific change with time. In FIG. 22, the start of irradiation of the ultraviolet ray for curing 54 (FIG. 1) is designated as a reference point of time (at zero).

Figure 22A:
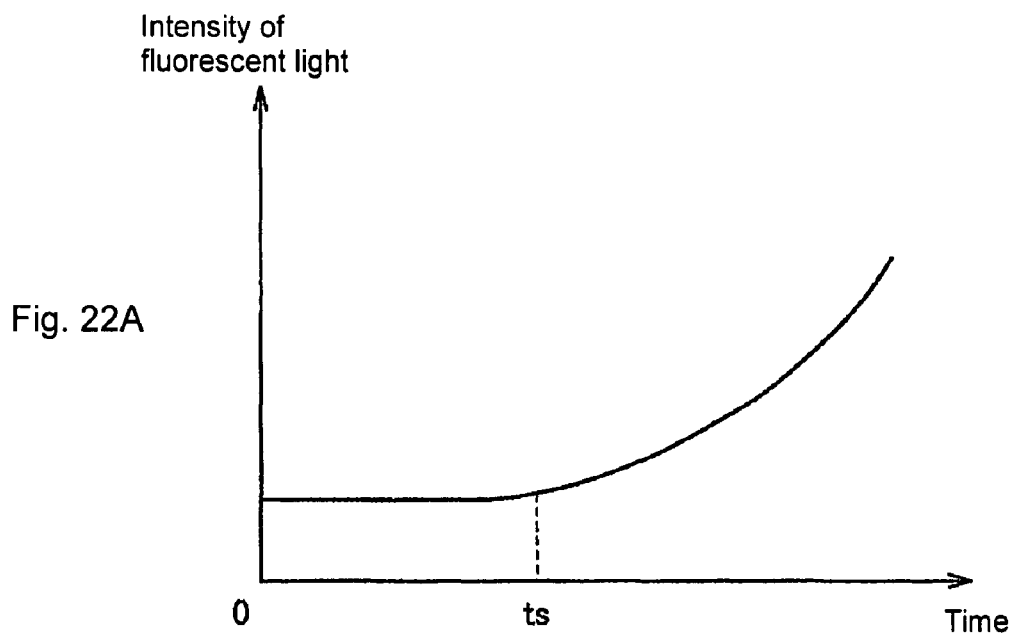
FIGS. 22A and 22B show diagrams illustrating estimation of a state of an ultraviolet curing resin material based on duration of time until occurrence of a particular change with time in the intensity of a fluorescent light.

FIG. 22A shows an example of the reference profile of a change with time which is predetermined.

Figure 22B:
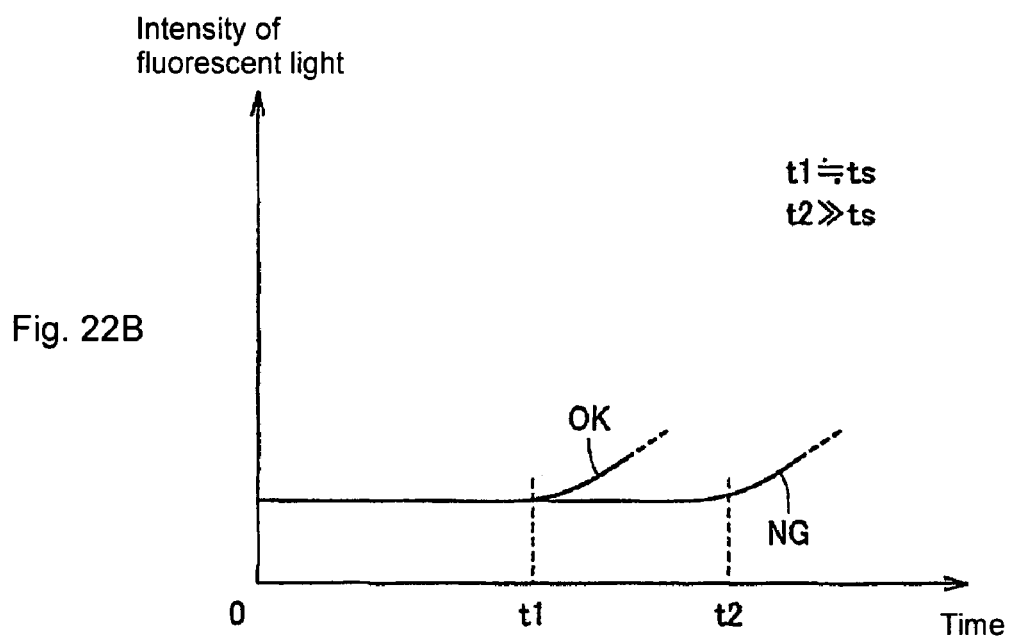

FIG. 22B shows a change with time in the intensity of the fluorescent light from the ultraviolet curing resin material under the same irradiation condition as of FIG. 22A.

Referring to FIG. 22A, the start of the increase of the intensity of the fluorescent light is referenced for determining a specific change with time and preliminarily designated to ts. The specific change with time may be timed with any particular moment, for example, when the increasing speed of the intensity is declined after the increase of the intensity, when the increase of the intensity stops, when the intensity starts declining after its increase, when a difference or ratio between two measurements of the intensity before and after the increase of the intensity exceeds a predetermined threshold, or when the intensity exceeds a predetermined threshold.

It is determined from FIG. 22B that the curing action of the ultraviolet curing resin material to be examined is normal when the intensity of the fluorescent light starts increasing at t1 (t1≅ts) after the start of the irradiation of the ultraviolet ray for curing (as denoted by OK). When the intensity of the fluorescent light starts increasing at t2 (t2>ts) after the start of the irradiation of the ultraviolet ray for curing (as denoted by NG), the curing action of the ultraviolet curing resin material may be not normal as determined.

The not normal curing action may include selection error of the type of the ultraviolet curing resin material, error of the weight of the ultraviolet curing resin material, deterioration in quality of the ultraviolet curing resin material, undesired progress of the curing action of the ultraviolet curing resin material during the storage, and variations of the irradiation condition (displacement of the ultraviolet ray irradiating head, discrepancy of the irradiation power, and mechanical failure).

Figure 23:
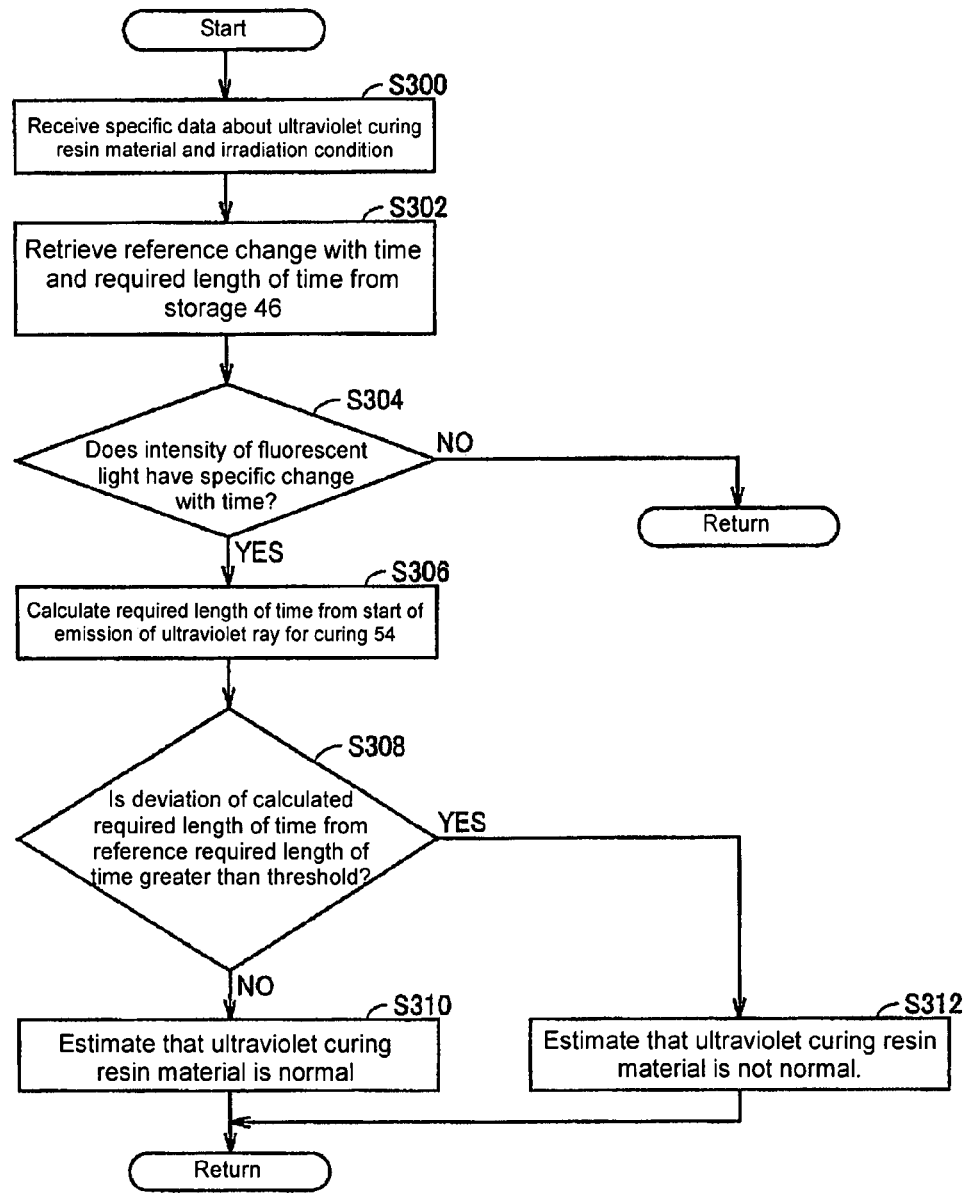
FIG. 23 shows a flowchart of estimation of a state of an ultraviolet curing resin material based on duration of time until occurrence of a particular change with time in the intensity of a fluorescent light.

FIG. 23 is a flowchart showing the procedure of estimating the state of the ultraviolet curing resin material from the length of time required for the intensity of the fluorescent light causing a specific change with time. The flowchart shown in FIG. 23 may be designated as a sub routine which is called at the estimating action (Step S14) shown in FIG. 13.

As shown in FIG. 23, the procedure starts with the CPU 40 receiving a specific data about the ultraviolet curing resin material and the irradiation condition from the user (Step S300) and retrieving the reference data of the length of time and the specific change with time in the intensity of the fluorescent light from the storage 46 in response to the specific data (Step S302). The CPU 40 then examines whether or not the current measurement of the intensity of the fluorescent light has a specific change with time (Step S304).

When the current measurement of the intensity of the fluorescent light has a specific change with time (YES at Step S304), the CPU 40 calculates the required length of time starting from the start of the irradiation of the ultraviolet ray for curing 54 (Step S306). The CPU 40 examines whether or not a deviation of the measurement from the reference length of time is greater than a predetermined threshold (Step S308). When the deviation of the measurement from the reference length of time is not greater than the predetermined threshold (NO at Step S308), the CPU 40 determines that the ultraviolet curing resin material to be examined is normal (Step S310). When the deviation of the measurement from the reference length of time is greater than the predetermined threshold (YES at Step S308), the CPU 40 determines that the ultraviolet curing resin material to be examined is not normal (Step S312) and returns to its preceding routine.

Meanwhile, when the current measurement of the intensity of the fluorescent light has no specific change with time (NO at Step S304), the CPU 40 returns to its preceding routine.

As described, the procedure of estimating the state of the ultraviolet curing resin material from the length of time required for the intensity of the fluorescent light causing a specific change with time allows any fault in the ultraviolet curing resin material to be identified through comparing the measurement of the length of time required for the intensity of the fluorescent light causing a specific change with time with its reference length. Accordingly, the yield of production can be improved while suppressing the amount of fault products.

(Estimation of the State of Ultraviolet Curing Resin Material Before and after Irradiation of Ultraviolet Ray for Curing)

In a production line, its productivity can be improved by estimating the state of the ultraviolet curing resin material before and after (the end on the irradiation of the ultraviolet ray for curing to determine the presence of any fault. More particularly, before the irradiation of the ultraviolet ray for curing, the ultraviolet curing resin material can readily be examined for pointing out selection error of the type of the ultraviolet curing resin material, error of the weight of the ultraviolet curing resin material, deterioration in quality of the ultraviolet curing resin material, or undesired progress of the curing action of the ultraviolet curing resin material during the storage. Also, after the irradiation of the ultraviolet ray for curing, the ultraviolet curing resin material can readily be examined for pointing out selection error of the type of the ultraviolet curing resin material, error of the weight of the ultraviolet curing resin material, deterioration in quality of the ultraviolet curing resin material, or under- or over-irradiation of the ultraviolet ray for curing.

Figure 24:
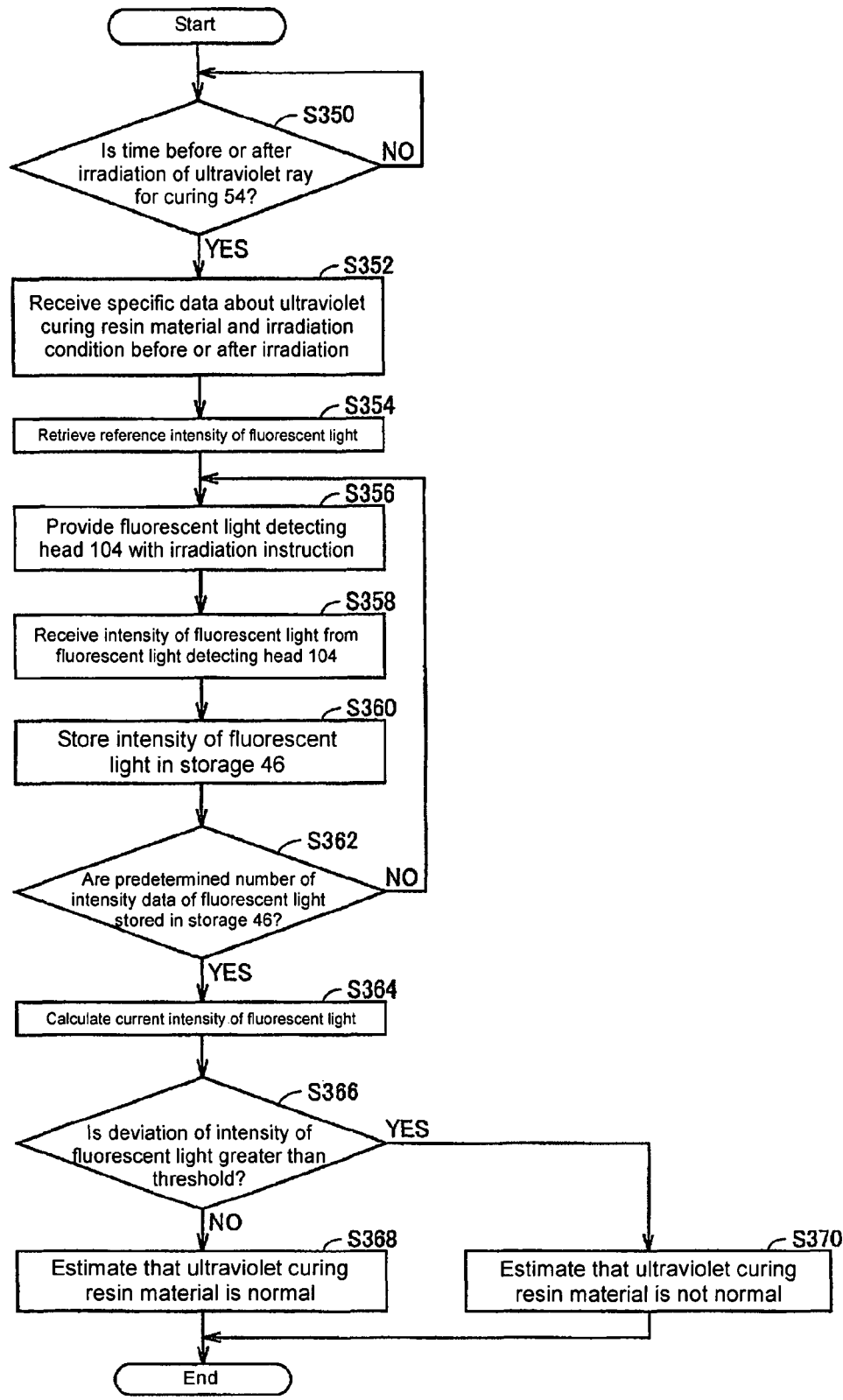
FIG. 24 shows a flowchart of estimation of a state of an ultraviolet curing resin material before and after irradiation of an ultraviolet ray for curing.

FIG. 24 is a flowchart showing the procedure of estimating the state of the ultraviolet curing resin material before and after the irradiation of the ultraviolet ray for curing.

As shown in FIG. 24, the procedure starts with the CPU 40 examining from an irradiation state signal received from the curing ultraviolet ray emitting apparatus 200 whether or not the state is before or after the irradiation of the ultraviolet ray for curing 54 (Step S350). The examination on either before or after may alternatively be predetermined by the user. When the state is not before nor after the irradiation of the ultraviolet ray for curing 54 (NO at Step S350), the CPU 40 stands by for before or after the irradiation of the ultraviolet ray for curing 54 (Step S350).

When the state is before or after the irradiation of the ultraviolet ray for curing 54 (YES at Step S350), the CPU 40 receives a specific data about the ultraviolet curing resin material and the irradiation condition before and after the irradiation of the ultraviolet ray for curing 54 (Step S352) and retrieves the reference of the intensity of the fluorescent light from the storage 46 in response to the deceived specific data (Step S354). The CPU 40 then provides the fluorescent light detecting head 104 with an irradiation instruction (Step S356). This is followed by the fluorescent light detecting head 104 emitting the detecting ultraviolet ray 50 to the ultraviolet curing resin material to be examined. The CPU 40 receives from the fluorescent light detecting head 104 a measurement of the intensity of the fluorescent light which is emitted from the photo polymerization initiator in the ultraviolet curing resin material upon irradiation of the ultraviolet ray for detection 50 (Step S358).

Then, the CPU 40 saves the measurement of the intensity of the fluorescent light in the storage 46 (Step S360) and examines whether or not a predetermined number of the measurements of the intensity of the fluorescent light are saved in the storage 46 (Step S362). When the predetermined number of the measurements of the intensity of the fluorescent light are not saved in the storage 46 (No at Step S362), the CPU 40 repeats the actions at Steps S356 to S362.

When the predetermined number of the measurements of the intensity of the fluorescent light are saved in the storage 46 (YES at Step S362), the CPU 40 retrieves the predetermined number of the measurements of the intensity of the fluorescent light from the storage 46 and conducts an averaging action to determine the calculated measurement (Step S364).

The CPU 40 further examine whether or not a deviation of the calculated measurement from a reference level of the intensity of the fluorescent light is greater than a threshold (Step S366). When the deviation of the calculated measurement from the reference level of the intensity of the fluorescent light is not greater than the threshold (NO at Step S366), the CPU 40 determines that the ultraviolet curing resin material is normal before or after the irradiation of the ultraviolet ray for curing 54 (Step S368). If the deviation of the calculated measurement from the reference level of the intensity of the fluorescent light is greater than the threshold (YES at Step S366), the CPU 40 determines that the ultraviolet curing resin material is not normal before or after the irradiation (Step S370). Then, the CPU 40 terminates its action.

As described, the procedure of estimating the state of the ultraviolet curing resin material before the start of the irradiation of the ultraviolet ray for curing allows the ultraviolet curing resin material to be examined for finding any fault prior to the start of the curing action. This prevents a redundancy of the irradiation of the curing ultraviolet ray 54 onto the ultraviolet curing resin material. Accordingly, the production efficiency at the production line can be improved.

As described, the procedure of estimating the state of the ultraviolet curing resin material after the irradiation of the ultraviolet ray for curing allows the ultraviolet curing resin material to be examined for finding any fault after the end of the curing action. Accordingly, under- or over-irradiation of the ultraviolet ray for curing 54 to the ultraviolet curing resin material can be detected.

(Estimation of Structural Stress in Ultraviolet Curing Resin Material from the Intensity of Fluorescent Light)

As described, the intensity of the fluorescent light is closely related to the degree of structural stress developed after the irradiation of the ultraviolet ray for curing in the ultraviolet curing resin material. In brief, the greater the accumulation of the structural stress in the ultraviolet curing resin material, the more the intensity of the fluorescent light will be declined. It is assumed that when the intensity of the fluorescent light is high after the irradiation of the ultraviolet ray for curing in the ultraviolet curing resin material, the structural stress accumulated becomes low.

Therefore, the structural stress in the fluorescent curing resin material can be estimated from the intensity of the fluorescent light measured after the irradiation of the ultraviolet ray for curing. The measurement of the structural stress can be used for examining whether the curing action of the ultraviolet curing resin material is successful or not. As the result, the ultraviolet curing resin material will be prevented from its defective, which may have a flaw or crack due to a failure of the curing action, mixing with any product.

Figure 25:
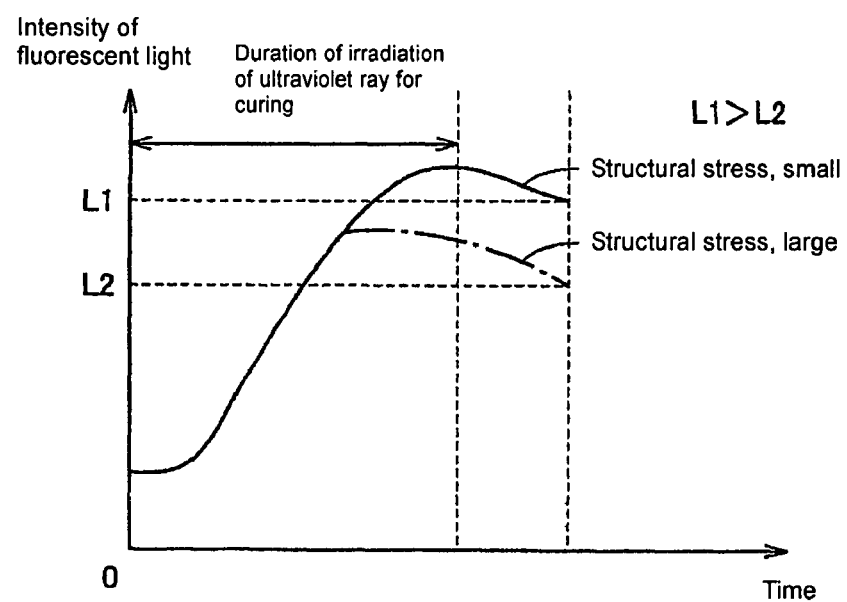
FIG. 25 shows a diagram illustrating estimation of structural stress in an ultraviolet curing resin material based on the intensity of a fluorescent light.

FIG. 25 illustrates a profile showing the estimation of structural stress in the ultraviolet curing resin material from the intensity of the fluorescent light. In FIG. 25, the start of irradiation of the ultraviolet ray for curing 54 (FIG. 1) is designated as a reference point of time (at zero).

It is estimated from FIG. 25 that the ultraviolet curing resin material where the intensity of the fluorescent light is L1 at the time when a given length of time has elapsed from the end of the irradiation of the ultraviolet ray for curing 54 is smaller in the structural stress than the ultraviolet curing resin material where the intensity of the fluorescent light is L2 (L1>L2).

It is found in most of the experiments that the intensity of the fluorescent light is increased with time (one or two days). This will be explained by the structural stress being eases with time. Accordingly, through measuring the intensity of the fluorescent light after the end of the irradiation of the ultraviolet ray for curing, the degree of easing the structural stress can be estimated.

The above described procedures for estimating the state all are provided for the purpose of illustration and may be modified depending on the type and usage of the ultraviolet curing resin material. More specifically, the procedures are not limited to the steps described but may be covered by the method for estimating the state according to the present invention even if one of them is separately executed.

It would be understood that the forgoing procedures of the embodied method for the present invention are illustrative but not of limitations. The scope of the present invention shall be limited by the appended claims of the present invention but not the description of the embodiment. The appended claims are then intended to cover all variations coming within the scope and spirit of the invention.

What is claimed is:

1. A method for estimating a state of an ultraviolet curing resin material including a main agent selected from at least one of a monomer and an oligomer, and a photo polymerization initiator, the method comprising:
    an irradiating step of irradiating an ultraviolet ray to the ultraviolet curing resin material, the ultraviolet curing resin material not containing a probe material;
    a detecting step of detecting a fluorescent light emitted from the photo polymerization initiator, the photo polymerization initiator not containing a probe material, when receiving the ultraviolet ray irradiated in the irradiating step; and
    an estimating step of estimating, via a state estimator comprising a processing unit, the state of the ultraviolet curing resin material based on the fluorescent light detected in the detecting step.

2. The method for estimating a state of an ultraviolet curing resin material according to claim 1, wherein
    the estimating step includes estimating the state of the ultraviolet curing resin material based on a change with time in intensity of the fluorescent light triggered by a curing action of the ultraviolet curing resin material during the irradiation of an ultraviolet ray for curing to cause the curing action of the ultraviolet curing resin material.

3. The method for estimating a state of an ultraviolet curing resin material according to claim 2, wherein
    the estimating step includes deciding that the photo polymerization initiator has substantially been consumed when the intensity of the fluorescent light after being increased is declined in an increasing speed, halted in the increase, or decreased.

4. The method for estimating a state of an ultraviolet curing resin material according to claim 2, wherein
    the estimating step includes deciding that the photo polymerization initiator has reached the maximum curing level when the intensity of the fluorescent light after being increased is declined in an increasing speed, halted in the increase, or decreased.

5. The method for estimating a state of an ultraviolet curing resin material according to claim 2, wherein
the estimating step includes deciding that the ultraviolet curing resin material has reached a particular curing level when a difference or ratio between intensities of the fluorescent light before and after a start of increase exceeds a predetermined threshold.

6. The method for estimating a state of an ultraviolet curing resin material according to claim 2, wherein
the estimating step includes deciding that the ultraviolet curing resin material has reached a particular curing level when the intensity of the fluorescent light exceeds a predetermined threshold.

7. The method for estimating a state of an ultraviolet curing resin material according to claim 2, wherein
the estimating step includes estimating the state of the ultraviolet curing resin material by comparing the change with time in the detected intensity of the fluorescent light and a change with time predetermined as a reference value.

8. The method for estimating a state of an ultraviolet curing resin material according to claim 2, wherein
the estimating step includes estimating the state of the ultraviolet curing resin material by obtaining duration of time from a particular reference time to occurrence of a particular change with time in the intensity of the fluorescent light, and comparing the obtained duration of time with a predetermined reference value.

9. The method for estimating a state of an ultraviolet curing resin material according to claim 1, wherein
the estimating step includes estimating the state of the ultraviolet curing resin material based on intensity of the fluorescent light detected before the irradiation of the ultraviolet ray for curing to cause a curing action of the ultraviolet curing resin material.

10. The method for estimating a state of an ultraviolet curing resin material according to claim 1, wherein
the estimating step includes estimating the state of the ultraviolet curing resin material based on intensity of the fluorescent light detected after the irradiation of the ultraviolet ray for curing to cause a curing action of the ultraviolet curing resin material.

11. The method for estimating a state of an ultraviolet curing resin material according to claim 1, wherein
the estimating step includes estimating a state of structural stress accumulated in the ultraviolet curing resin material based on intensity of the fluorescent light detected in the ultraviolet curing resin material after realizing a curing action.

12. The method for estimating a state of an ultraviolet curing resin material according to claim 1, wherein
the irradiating step includes irradiating an ultraviolet ray for detection to detect the fluorescent light emitted from the photo polymerization initiator and periodically being changed in intensity, and
the detecting step includes:
a light receiving sub step of receiving a light emitted from the ultraviolet curing resin material; and
an extracting sub step of extracting from the light received in the light receiving step, as the fluorescent light, a periodic component corresponding to a period of change in the intensity of the ultraviolet ray for detection.

13. The method for estimating a state of an ultraviolet curing resin material according to claim 12, wherein
the ultraviolet ray for curing has substantially constant intensity with time, and
the ultraviolet ray for detection is emitted in a predetermined period and has intensity of light in a pulse form.

* * * * *